US007635569B2

(12) United States Patent
Thomas et al.

(10) Patent No.: US 7,635,569 B2
(45) Date of Patent: Dec. 22, 2009

(54) PROTEIN/SOLUBILITY FOLDING ASSESSED BY STRUCTURAL COMPLEMENTATION

(75) Inventors: Philip Jordan Thomas, Dallas, TX (US); John F. Hunt, New York, NY (US); William Christian Wigley, Dallas, TX (US); Rhesa D. Stidham, Dallas, TX (US)

(73) Assignees: Board of Regents, The University of Texas System, Austin, TX (US); Trustees of Columbia University in the City of New York, New York, NY (US)

( * ) Notice: Subject to any disclaimer, the term of this patent is extended or adjusted under 35 U.S.C. 154(b) by 106 days.

(21) Appl. No.: 11/617,191

(22) Filed: Dec. 28, 2006

(65) Prior Publication Data

US 2007/0178498 A1 Aug. 2, 2007

Related U.S. Application Data

(60) Continuation of application No. 10/748,720, filed on Dec. 30, 2003, now Pat. No. 7,455,978, which is a division of application No. 09/775,051, filed on Jan. 31, 2001, now Pat. No. 6,727,070.

(60) Provisional application No. 60/182,283, filed on Feb. 14, 2000.

(51) Int. Cl.
*G01N 33/53* (2006.01)
*C07H 21/04* (2006.01)

(52) U.S. Cl. ........................................ 435/7.1; 536/23.4

(58) Field of Classification Search ....................... None
See application file for complete search history.

(56) References Cited

U.S. PATENT DOCUMENTS

| 5,120,653 | A | 6/1992 | Henderson | 435/252.33 |
|---|---|---|---|---|
| 6,294,330 | B1 | 9/2001 | Michnick et al. | 435/6 |
| 6,727,070 | B2 | 4/2004 | Thomas et al. | 435/7.1 |

FOREIGN PATENT DOCUMENTS

| WO | WO 98/34120 | 8/1998 |
|---|---|---|
| WO | WO 98/44350 | 10/1998 |

OTHER PUBLICATIONS

Abbas-Terki and Picard, "α-Complemented β-galactosidase. An in vivo model substrate for the molecular chaperone heat-shock protein 90 in yeast," *Eur. J. Biochem.*, 266:517-523, 1999.
Betton et al., "Probing the structural role of an αβ loop of maltose-binding protein by mutagenesis: heat-shock induction by loop variants of the maltose-binding protein that form periplasmic inclusion bodies," *J. Mol. Biol.*, 262(2):140-150, 1996.
Blackwell and Horgan, "A novel strategy for production of a highly expressed recombinant protein in an active form," *FEBS Lett.*, 295:10-12, 1991.
Blakely et al., "Epidermal growth factor receptor dimerization monitored in live cells," *Nature Biotech*, 18:218-222, 2000.
Bourot et al., "Glycine betaine-assisted protein folding in a *lysA* mutant of *Escherichia coli.*,". *J Biol. Chem.*, 275:1050-1056, 2000.
Brown et al., "Correcting temperature-sensitive protein folding defects," *J. Clin. Invest.*, 99:1432-1444, 1997.
Bruijn et al., "Aggregation and motor neuron toxicity of an ALS-linked SOD1 mutant independent from wild-type SOD1," *Science*, 281:1851-1853, 1998.
Culvenor et al., "Subcellular localization of the Alzheimer's disease amyloid precursor protein and derived polypeptides expressed in a recombinant yeast system," *Amyloid: Int J Exp Clin Invest*, 5(2):79-89, 1998.
Dobson, "Protein misfolding, evolution and disease," *TIBS* 24:329-332, 1999.
Farzaneh et al., *Nucleic Acids Res.*, 16:11319-11325, 1988.
Foster et al., "Pharmacological rescue of mutant p53 conformation and function," *Science*, 286:2507-2510, 1999.
Harper and Lansbury Jr., "Models of amyloid seeding in Alzheimer's disease and scrapie: mechanistic truths and physiological consequences of the time-dependent solubility of amyloid proteins," *Annu. Rev. Biochem.*, 66:385-407, 1997.
Houry et al., "Identification of in vivo substrates of the chaperonin GroEL," *Nature*, 402:147-154, 1999.
Huang et al., "NMR structure and mutagenesis of the Fas (APO-1/CD95) death domain," *Nature*, 384:638-641, 1996.
Hung et al., "Crystal structure of the ATP-binding subunit of an ABC transporter," *Nature*, 396:703-707, 1998.
Huth et al., "Design of an expression system for detecting folded protein domains and mapping macromolecular interactions by NMR," *Protein Sci.*, 6:2359-2364, 1997.
Johnsson and Varshavsky, "Split ubiquitin as a sensor of protein interactions in vivo," *Proc. Natl. Acad. Sci. USA*, 91:10340-10344, 1994.
Kapust and Waugh, "*Escherichia coli* maltose-binding protein is uncommonly effective at promoting the solubility of polypeptides to which it is fused," *Protein Science*, 8:1668-1674, 1999.
King and Sorscher, "Recombinant synthesis of cystic fibrosis transmembrane conductance regulator and functional nucleotide-binding domains," *Methods Enzymol.*, 292:686-697, 1998.

(Continued)

*Primary Examiner*—Nancy Vogel
(74) *Attorney, Agent, or Firm*—Fulbright & Jaworski

(57) ABSTRACT

Many proteins, when produced recombinantly, suffer from improper processing, folding and lack normal solubility. Modified proteins, including those indicative of disease states, also can have such defects. The present invention is directed to methods of identifying proper and improper protein folding, aberrant processing and/or insolubility. The method relies on the use of two components: a specialized fusion protein and structural complementation. The fusion protein contains sequences from the protein of interest and one portion of a marker protein that, by itself, is not active. A host cell then provides the remainder of the marker protein that serves to "complement" the function of the fused marker protein such that their association restores activity, permitting detection.

6 Claims, 2 Drawing Sheets

OTHER PUBLICATIONS

Ko et al., "The cystic fibrosis transmembrane conductance regulator," *J. Biol. Chem.*, 268:24330-24338, 1993.

Lee et al., "Effect of the N-terminal hydrophobic sequence of hepatitis B virus surface antigen on the folding and assembly of hybrid β-galactosidase in *Escherichia coli*," *Eur. J. Biochem.*, 187:417-424, 1990.

Luzzago and Cesareni, "Isolation of point mutations that affect the folding of the H chain of human ferritin in *E. coli*," *EMBO J*, 8:569-576, 1989.

Maxwell et al., "A simple in vivo assay for increased protein solubility," *Protein Science*, 8:1908-1911, 1999.

Nixon and Benkovic, "Improvement in the efficiency of formyl transfer of a GAR transformylase hybrid enzyme," *Protein Engineering*, 13(5);323-327, 2000.

Opal and Paulson, "Genetic instabilities and hereditary neurological diseases," *Am J. Hum. Genet.*, 63(6):1921, 1998.

Papouchado et al., "Expression of properly folded human glutamate decarboxylase 65 as a fusion protein in *Escherichia coli*," *Eur. J. Biochem.*, 246:350-359, 1997.

Pelletier et al., "An invivo library-versus-library selection of optimized protein-protein interactions," *Nature Biotech*, 17:683-690, 1999.

Qu and Thomas, "Alteration of the cystic fibrosis transmembrane conductance regulator folding pathway," *J. Biol. Chem.*, 271(13):7261-7264, 1996.

Rao et al., "Rhodopsin mutation G9OD and a molecular mechanism for congenital night blindness," *Nature*, 367:639-642, 1994.

Rossi et al., "Monitoring protein-protein interactions in intact eukaryotic cells by beta-galactosidase complementation," *Proc. Natl. Acad. Sci. USA*, 94:8405-8410, 1997.

Sugihara and Baldwin, "Effects of 3' end deletions from Vibrio hrveyi luxB gene on luciferase subunit folding and enzyme assembly: generation of temperature-sensitive polypeptide folding mutants," *Biochemistry*, 27:2872-2880, 1988.

Tan and Pepys, "Amyloidosis," *Histopathology*, 25:403-414, 1994.

Thomas et al., "Altered protein folding may be the molecular basis of most cases of cystic fibrosis," *FEBS Lett.*, 312:7-9, 1992.

Thomas et al., "Defective protein folding as a basis of human disease," *TIBS*, 20:456-459, 1995.

Valois et al., "Utilisation of the PCA strategy to study the folding of the RBD of raf," *FASEB Journal*, 13:A1387, 330, 1999.

Waldo et al., "Rapid protein-folding assay using green fluorescent protein," *Nature Biotechnology*, 17:691-695, 1999.

Wang et al., "Expression and purification of the first nucleotide-binding domain an dlinker region of human multidrug resistance gene product: comparison of fusions to glutathione S-transferase, thioredoxin and maltose-binding protein," *Biochem J.*, 338:77-81, 1999.

Wigley et al., "Protein solubility and folding monitored in vivo by structural complementation of a genetic marker protein," *Nature Biotechnology*, 19:131-136, 2001.

Wood et al., "Prolines and amyloidogenicity in fragments of the Alzheimer's peptide β/A4," *Biochemistry*, 34(3):724-730, 1995.

SEQUENCE LISTING

```
<160> NUMBER OF SEQ ID NOS: 3

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
gatgctcaac ggtgacttta ggatcggtat cttctcgaat ttc                        43

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
caacggtgac tttaatatcg gtatctttct cg                                    32

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
ggtgacttta ggtccggtat ctttctcg                                         28
```

PROTEIN/SOLUBILITY FOLDING ASSESSED BY STRUCTURAL COMPLEMENTATION

This application is a continuation of U.S. patent application Ser. No. 10/748,720 filed on Dec. 30, 2003, now U.S. Pat. No. 7,455,978 issued on Nov. 25, 2008, which is a divisional of U.S. patent application Ser. No. 09/775,051 filed Jan. 31, 2001, now U.S. Pat. No. 6,727,070 issued on Apr. 27, 2004, which claims priority to U.S. Provisional Patent Application No. 60/182,283 filed Feb. 14, 2000, the entire contents of each are incorporated herein by reference. Additionally, all patents, published patent applications, and other references cited throughout this specification are hereby incorporated by reference in their entireties. This invention was made with government support under Grant No. DK49835 awarded by The National Institutes of Health. The government has certain rights in the invention.

The invention disclosed herein was made with the support of the U.S. Government under The National Institutes of Health Grant DK49835.

BACKGROUND OF THE INVENTION

1. Field of the Invention

The present invention relates to the fields of biochemistry, cellular biology and molecular biology. More particularly, it relates to the field of protein biochemistry, and specifically, to the use of an assay for determining protein folding and solubility.

2. Description of Related Art

There are a wide variety of potential applications for a genetic system enabling rapid and efficient evaluation of protein solubility characteristics in vivo. One of the cornerstones of biotechnology is the ability to express target proteins in functional form in vivo in genetically-engineered organisms. However, many important target proteins are not efficiently expressed in soluble form in bacteria such as E. coli, due at least in part to the complexity of the protein folding process in vivo (Houry et al., 1999). When encountering a target protein that fails to be expressed in soluble form in vivo, the yield of soluble protein can often be improved by optimizing various factors such as the primary sequence of the target protein (Huang et al., 1996) or the genetic background or growth conditions of the bacterium (lung et al., 1998; Brown et al., 1997; Blackwell & Horgan, 1991; Bourot et al., 2000; Sugihara & Baldwin, 1988; Wynn et al., 1992). However, existing assays for protein expression in soluble form are tedious, usually requiring lysis and fractionation of cells followed by protein analysis by SDS-polyacrylamide gel electrophoresis. Using this traditional approach, screening for protein constructs and/or physiological conditions yielding improved solubility is inefficient, and genetic selection is impossible.

Protein folding diseases represent a second area in which protein solubility characteristics are of vital medical and technological importance (Thomas et al., 1995; Dobson, 1999). These diseases, which have proven particularly refractory to pharmaceutical development, are caused either by misfolding of a protein during biosynthesis subsequent to acquiring some mutation (Brown et al., 1997; Thomas et al., 1992; Rao et al., 1994) or by aberrant protein processing leading to the formation of an aggregation-prone product, such as the peptide forming the amyloid plaques associated with Alzheimer's disease (Tan & Pepys, 1994; Harper & Lansbury, 1997), SOD1 in amyotropic lateral sclerosis (Bruijn et al., 1998), α-synuclein in Parkinson's disease (Galvin et al., 1983), amyloid A and P deposits in systemic amyloidosis (Hind et al., 1983), transthyretin fibrils in fatal familial insomnia (Colon & Kelly, 1992) and the intranuclear inclusions associated with polyglutamine expansions which cause Huntington's disease (Martin & Gusella, 1986; HDCRG, 1993; Davies et al., 1997), spinocerebellar ataxia (Wells & Warren, 1998), spinobulbar muscular atrophy (La Spada et al., 1991), and Machado-Joseph Disease (Kawaguchi et al., 1994). The ability to rapidly and efficiently screen for protein solubility in vivo could also be applied to the development of assays for pharmaceutical compounds preventing the misfolding or aggregation of proteins involved in protein folding diseases (i.e., assays for compounds that prevent precipitation of such aggregation-prone proteins).

Thus, there remains a need in the field for improved methods of screening for protein folding and solubility.

SUMMARY OF THE INVENTION

The present invention involves the use of a genetic system based on structural complementation (Richards & Vithayati, 1959; Ullmann et al., 1967; Taniuichi & Anfinsen, 1971; Zabin & Villarejo, 1975; Pecorari et al., 1993; Schonberger et al., 1996) of a selectable marker protein can be used as the basis of a direct in vivo solubility assay. Structural complementation involves the division of a protein into two component segments which must be combined to form a stable and fully functional structure. The specific implementation of the method is an adaptation of the classic α-complementation system of β-galactosidase (β-gal) (Ullmann et al., 1967). However, the same concept could potentially be applied to other selectable genetic markers like chloramphenicol transacetylase or even screenable markers like the green fluorescent protein (although appropriately complementing fragments of these proteins would have to be developed first). β-gal can be divided into two fragments (α and ω) capable of associating with each other to form an active enzyme (Ullmann et al., 1967). Redistribution of the α-fragment from the soluble to the insoluble fraction in E. coli cells leads to a reduction in the level of β-gal activity which can be assayed either during growth on indicator agar plates using the chromogenic substrate X-gal, or in suspension culture. Fusion of the α-fragment to the C-terminus of a target protein leads to the formation of a chimeric protein with solubility properties similar to that of the target protein alone. Thus, β-gal activity levels report the solubility of the target fusion. By contrast, three extant systems for monitoring solubility and misfolding in vivo rely on the use of fusions with the full-length maker proteins β-gal (Lee et al., 1990), GFP (Waldo et al., 1999) and CAT (Maxwell et al., 1999). It is well documented that the solubility properties of protein fusions to intact marker enzymes tend to be dominated by the solubility properties of the marker enzyme, as evidenced by the use of MBP (Ko et al., 1993; Kapust et al., 1999), thioredoxin (Papouchado et al., 1997), and GST (Wang et al., 1999) fusions to enhance the solubility of some otherwise insoluble protein constructs. Such a colorimetric plate assay should be readily adapted to efficient high-throughput screening.

Thus, there is provided, a method for assessing protein folding and/or solubility comprising (a) providing an expression construct comprising (i) a gene encoding fusion protein, said fusion protein comprising a protein of interest fused to a first segment of a marker protein, wherein said first segment does not affect the folding or solubility of the protein of interest, and (ii) a promoter active in said host cell and operably linked to said gene, (b) expressing said fusion protein in a host cell that also expresses a second segment of said marker protein, wherein said second segment is capable of structural complementation with said first segment, and (c) determining structural complementation, wherein a greater degree of structural complementation, as compared to structural complementation observed with appropriate negative controls, indicates proper folding and/or solubility of said protein.

The fusion may be N- or C-terminal to said protein of interest. The marker protein may be selected from the group consisting of a target binding protein, an enzyme, a protein inhibitor, and a chromophore. Examples include ubiquitin, green fluorescent protein, blue fluorescent protein, yellow fluorescent protein, luciferase, aquorin, β-galactosidase, cytochrome c, chymotrypsin inhibitor, RNase, phosphoglycerate kinase, invertase, staphylococcal nuclease, thioredoxin C, lactose permease, amino acyl tRNA synthase, and dihydrofolate reductase. In the particular case of β-galactosidase, the first segment is the ω-peptide of β-galactosidase, and said second segment is the ω-peptide of β-galactosidase. In certain embodiments the marker protein is associated with a detectable phenotype, including enzymatic activity, chromophore or fluorophore activity.

The protein of interest may be Alzheimer's amyloid peptide (Aβ), SOD1, presenillin 1 and 2, α-synuclein, amyloid A, amyloid P, CFTR, transthyretin, amylin, lysozyme, gelsolin, p53, rhodopsin, insulin, insulin receptor, fibrillin, α-ketoacid dehydrogenase, collagen, keratin, PRNP, immunoglobulin light chain, atrial natriuretic peptide, seminal vesicle exocrine protein, β2-microglobulin, PrP, precalcitonin, ataxin 1, ataxin 2, ataxin 3, ataxin 6, ataxin 7, huntingtin, androgen receptor, CREB-binding protein, dentaorubral pallidoluysian atrophy-associated protein, maltose-binding protein, ABC transporter, glutathione S transferase, and thioredoxin.

The gene encoding the second segment may be carried on a chromosome of said host cell or episomally. The host cell may be a bacterial cell, an insect cell, a yeast cell, a nematode cell, and a mammalian cell. Examples include *E. coli, C. elegans*, or *S. fugeria*, and a variety of mammalian cells. Preferred promoters include Taq promoter; T7 promoter, or $P_{lac}$ promoter (bacterial), CupADH, Gal (yeast) or PepCk or tk (mammalian).

In particular embodiment, the method utilizes a negative control that is a host cell lacking the second segment of said marker protein and/or a fusion protein that is improperly folded and/or insoluble.

In another embodiment, there is provided, a method for screening protein folding and/or solubility mutants comprising (a) providing a gene encoding fusion protein comprising (i) a protein of interest and (ii) a first segment of a marker protein, wherein said first segment does not affect the folding or solubility of the protein of interest, wherein said fusion protein is not properly folded and/or soluble when expressed in said host cell, and (ii) a promoter active in said host cell and operably linked to said gene, wherein said fusion protein is not properly folded and/or soluble when expressed in said host cell, (b) mutagenizing that portion of the gene encoding said protein of interest, (c) expressing said fusion protein in a host cell that expresses a second segment of said marker protein, wherein said second segment is capable of structural complementation with said first segment, and (d) determining structural complementation, wherein a relative increase in structural complementation, as compared to the structural complementation observed with the unmutagenized fusion protein, indicates an increase in proper folding and/or solubility of said protein.

In yet another embodiment, there is provided a method for screening candidate modulator substance that modulates protein folding and/or solubility comprising (a) providing an expression construct comprising (i) a gene encoding fusion protein, said fusion protein comprising a protein of interest fused to a first segment of a marker protein, wherein said first segment does not affect the folding or solubility of the protein of interest, and (ii) a promoter active in said host cell and operably linked to said gene, (b) expressing said fusion protein in a host cell that expresses a second segment of said marker protein, wherein said second segment is capable of structural complementation with said first segment, (c) contacting the host cell with said candidate modulator substance; and (d) determining structural complementation, wherein a relative change in structural complementation, as compared to the structural complementation observed in the absence of said candidate modulator substance, indicates that said candidate modulator substance is a modulator of protein folding and/or solubility. The candidate modulator substance may be a protein, a nucleic acid or a small molecule.

Following long-standing patent language convention, the terms "a" or "an," when used in conjunction with "comprising," may mean one or more than one, herein the description and claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) A schematic depicting the complementation solubility assay. P (squares) represents the target protein, and α (triangles) and ω (trapezoids) represent each of the complementing fragments of the tetrameric β-galactosidase. Brackets indicate the concentration dependence of the assay regarding the availability of soluble (folded) target/α fusion. $K_d$ is indicated solely to highlight the concentration-dependent equilibrium association/dissociation reaction. (FIG. 1B) A schematic representation of the target protein/α-fragment C-terminal fusion expression construct (α-fragment, residues 7-58 from full length β-galactosidase. "HA" indicates the position of the inserted influenza hemagglutinin (HA) immuno-tag (residue sequence YPYD-VPDYA) (SEQ ID NO. 4) present in some of the constructs examined.

DESCRIPTION OF ILLUSTRATIVE EMBODIMENTS

Figure 1A:
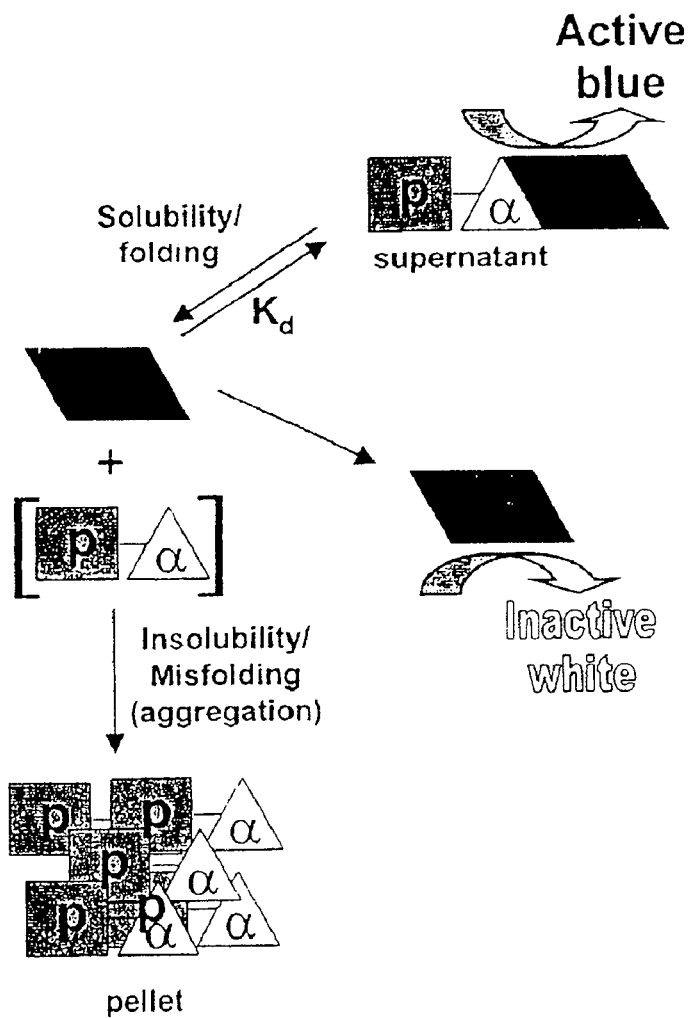
FIGS. 1A and 1B: An in vivo solubility assay based on structural complementation.

Protein misfolding is the basis of a number of human diseases. It also presents a sizable obstacle to the production of functional recombinant proteins. In addition, there is a tremendous potential to modulate in vivo function of proteins by modulating protein folding. To date, the study of misfolding and its circumvention has required development of specific assays for each individual case.

However, for maximum utility, such a method should provide an easily measured signal, be sensitive to subtle changes in the solubility of the target protein over a wide concentration range, allow phenotypic selection of the soluble protein, and have minimal effect on the solubility of the target protein. The present invention offers each of these advantages.

The present invention utilizes generalized fusion constructs and the phenomenon of "structural complementation" to examine protein folding and/or solubility in cell- or organism-based screening. In a particular embodiment, the α and ω peptides of β-galactosidase are used, the first as a fusion partner for a given protein of interest, in a complementation assay. Where the protein of interest is properly folded, the fusion remains soluble and can associate the other peptide of β-galactosidase, permitting enzyme activity and detection. A variety of different host cells, "structural complementation" pairs (enzymes, binding proteins, chromophores) and target proteins can be used.

The studies presented herein demonstrate that this system reliably reports on the solubility of eight fused target proteins: the maltose binding protein and mutants thereof, the first nucleotide binding domains of the cystic fibrosis transmembrane conductance regulator and the branched chain amino acid transporter from the hyperthermophilic archeon *methanococcus jannaschii*, and the Aβ peptide of the Alzheimer's precursor protein. The fact that the signal produced by the fusions is proportional to the solubility of the nucleotide binding domain targets when expressed without the α-fragment indicates that this relatively small polypeptide does not significantly effect the solubility of the target protein, unlike fusions to a larger marker protein (e.g., MBP, Harper and Lansbury, 1997). This could provide a significant advantage over two recently reported solubility monitoring systems that rely on fusions with larger soluble proteins, namely full length β-gal (Lee et al., 1990), GFP (Waldo et al., 1999) and CAT (Maxwell et al., 1999). It is well-documented that fusions with highly soluble proteins such as GST (Wang et al., 1999), MBP (Ko et al., 1993), and thioredoxin (Papouchado et al., 1997), and the immunoglobulin binding domain (GB1) (Huth et al., 1997) significantly improve the solubility properties of a variety of expressed proteins. Thus, it is reasonable to expect that in some cases, GFP and CAT may have a significant effect on the solubility of the target.

As mentioned above, this system has several potential uses. For example, recombinant production systems can be tested to determine if the polypeptide to be produced is properly folded. In addition, target proteins may be diagnostic of disease states. The system also could find utility in the development and selection of bacterial strains particularly effective at expressing and folding heterologous proteins, or for phenotypic selection of a wide variety of proteins in their study by random mutagenesis. These powerful approaches currently are limited to proteins which themselves are required for a measurable cellular function. Thus, the present solubility detection system provides an important avenue for understanding fundamental biological processes such as how primary sequence directs the formation of a unique three-dimensional structure, or the identity and mechanisms of cellular systems important for efficient protein maturation.

One aspect of the invention is the minimal impact of the fusion partners on the protein of interest. The presence of only "systematic" effects (i.e., similar both in the presence and absence of either drug or mutation) on the solubility of the target permits ready comparison. This actually provides the added advantage of being able to adjust the sensitivity of the assay depending on the target protein of interest. Recent discovery of mutations in the α subunit permit "tuning" of the α-θ interaction which also can be used for altering the sensitivity.

Perhaps the most exciting application of the system is the discovery of drugs which modulate the folding of disease related proteins. Previously, the search for pharmaceuticals has focused on the identification of compounds which inhibit cellular processes. However, the increasing prevalence of diseases associated with protein misfolding such as Huntington's disease, Alzheimer's disease, Parkinson's disease, cystic fibrosis, amyotropic lateral schlerosis, Creutzfeld-Jacob disease, and some forms of diabetes and cancer presents a new challenge for the pharmaceutical industry. The identification of drugs which target proteins with a propensity to misfold requires the development of novel screening and assay methodologies such as the α-complementation system described herein. Encouraging evidence that such pharmaceuticals may be identified has recently been provided by Rastinejad and co-workers (Foster et al., 1999) who reported the identification of a class of compounds which stabilized a folding mutant of p53 in a soluble and functional conformation, thereby rescuing its ability to prevent tumor growth in mice.

Various aspects of the invention are described, in greater detail, in the following pages.

A. PROTEIN FOLDING AND MUTANT PROTEINS

Several diseases, such as Alzheimer's disease, Parkinson's disease, Huntington's disease, and others are thought to be the result of, or associated with misfolding in vivo. In certain embodiments, the present invention provides a method of assaying for the presence of protein misfolding in a living cell.

Proteins expressed through recombinant means often misfold, particularly in prokaryotic host cells that lack the processing machinery of an eukaryotic cell. When a protein misfolds, it often becomes less soluble, and may precipitate in the cell as an inclusion body. Additionally, mutations in naturally occurring proteins increase the rate of misfolding when endogenously expressed, as well as when exogenously expressed in a recombinant host cell. In certain embodiments, the present invention allows various mutations, whether natural or produced by the hand of man, to be assayed for their ability to increase or decrease protein misfolding in vivo.

1. Fusion Proteins

An aspect of the present invention is the discovery that peptides, polypeptides or proteins, useful for alpha complementation, may be joined to a larger soluble protein, polypeptide or peptide, wherein the folding reaction is dominated by the soluble protein, polypeptide or peptide. The soluble protein, peptide or polypeptide may have the same length or amino acid sequence as the endogenously produced protein, polypeptide or peptide. In other embodiments, the soluble protein, peptide or polypeptide may be a truncated protein, protein domain or protein fragment of a larger peptide chain. For example, the folding of the soluble fragments of a membrane embedded or otherwise hydrophobic protein may be used to create a fusion protein.

Fusion proteins are produced by operatively linking at least one nucleic acid encoding at least one amino acid sequence to at least a second nucleic acid encoding at least a second amino acid sequence, so that the encoded sequences are translated as a contiguous amino acid sequence either in vitro or in vivo. Fusion protein design and expression is well known in the art, and methods of fusion protein expression are described herein, and in references, such as, for example, U.S. Pat. No. 5,935,824, incorporated herein by reference.

In certain embodiments, a peptide, polypeptide or protein may be joined at or near the N-terminal or C-terminal end of a soluble protein, peptide or polypeptide. In certain embodiments, it is contemplated that the alpha complementing peptide or polypeptide may be attached to the soluble protein, peptide or polypeptide via a linker moiety. One such linker is another peptide, such as described in U.S. Pat. No. 5,990,275, incorporated herein by reference.

2. Mutagenesis

Where employed, mutagenesis will be accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

a. Random Mutagenesis i) Insertional Mutagenesis

Insertional mutagenesis is based on the inactivation of a gene via insertion of a known DNA fragment. Because it involves the insertion of some type of DNA fragment, the mutations generated are generally loss-of-function, rather than gain-of-function mutations. However, there are several examples of insertions generating gain-of-function mutations (Oppenheimer et al. 1991). Insertion mutagenesis has been very successful in bacteria and *Drosophila* (Cooley et al. 1988) and recently has become a powerful tool in corn (Schmidt et al. 1987); *Arabidopsis*; (Marks et al., 1991; Koncz et al. 1990); and *Antirrhinum* (Sommer et al. 1990).

Transposable genetic elements are DNA sequences that can move (transpose) from one place to another in the genome of a cell. The first transposable elements to be recognized were the Activator/Dissociation elements of *Zea mays*. Since then, they have been identified in a wide range of organisms, both prokaryotic and eukaryotic.

Transposable elements in the genome are characterized by being flanked by direct repeats of a short sequence of DNA that has been duplicated during transposition and is called a target site duplication. Virtually all transposable elements whatever their type, and mechanism of transposition, make such duplications at the site of their insertion. In some cases the number of bases duplicated is constant, in other cases it may vary with each transposition event. Most transposable elements have inverted repeat sequences at their termini. these terminal inverted repeats may be anything from a few bases to a few hundred bases long and in many cases they are known to be necessary for transposition.

Prokaryotic transposable elements have been most studied in *E. coli* and Gram negative bacteria, but also are present in Gram positive bacteria. They are generally termed insertion sequences if they are less than about 2 kB long, or transposons if they are longer. Bacteriophages such as mu and D108, which replicate by transposition, make up a third type of transposable element. elements of each type encode at least one polypeptide a transposase, required for their own transposition. Transposons often further include genes coding for function unrelated to transposition, for example, antibiotic resistance genes.

Transposons can be divided into two classes according to their structure. First, compound or composite transposons have copies of an insertion sequence element at each end, usually in an inverted orientation. These transposons require transposases encoded by one of their terminal IS elements. The second class of transposon have terminal repeats of about 30 base pairs and do not contain sequences from IS elements.

Transposition usually is either conservative or replicative, although in some cases it can be both. In replicative transposition, one copy of the transposing element remains at the donor site, and another is inserted at the target site. In conservative transposition, the transposing element is excised from one site and inserted at another.

Eukaryotic elements also can be classified according to their structure and mechanism of transportation. The primary distinction is between elements that transpose via an RNA intermediate, and elements that transpose directly from DNA to DNA.

Elements that transpose via an RNA intermediate often are referred to as retrotransposons, and their most characteristic feature is that they encode polypeptides that are believed to have reverse transcriptionase activity. There are two types of retrotransposon. Some resemble the integrated proviral DNA of a retrovirus in that they have long direct repeat sequences, long terminal repeats (LTRs), at each end. The similarity between these retrotransposons and proviruses extends to their coding capacity. They contain sequences related to the gag and pol genes of a retrovirus, suggesting that they transpose by a mechanism related to a retroviral life cycle. Retrotransposons of the second type have no terminal repeats. They also code for gag- and pol-like polypeptides and transpose by reverse transcription of RNA intermediates, but do so by a mechanism that differs from that or retrovirus-like elements. Transposition by reverse transcription is a replicative process and does not require excision of an element from a donor site.

Transposable elements are an important source of spontaneous mutations, and have influenced the ways in which genes and genomes have evolved. They can inactivate genes by inserting within them, and can cause gross chromosomal rearrangements either directly, through the activity of their transposases, or indirectly, as a result of recombination between copies of an element scattered around the genome. Transposable elements that excise often do so imprecisely and may produce alleles coding for altered gene products if the number of bases added or deleted is a multiple of three.

Transposable elements themselves may evolve in unusual ways. If they were inherited like other DNA sequences, then copies of an element in one species would be more like copies in closely related species than copies in more distant species. This is not always the case, suggesting that transposable elements are occasionally transmitted horizontally from one species to another.

ii) Chemical Mutagenesis

Chemical mutagenesis offers certain advantages, such as the ability to find a full range of mutant alleles with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the 04 position of thymine induced by exposure to n-nitrosoureas results in TA to CG transitions.

A high correlation between mutagenicity and carcinogenity is the underlying assumption behind the Ames test (McCann et al., 1975) which speedily assays for mutants in a bacterial system, together with an added rat liver homogenate, which contains the microsomal cytochrome P450, to provide the metabolic activation of the mutagens where needed.

In vertebrates, several carcinogens have been found to produce mutation in the ras proto-oncogene. N-nitroso-N-methyl urea induces mammary, prostate and other carcinomas in rats with the majority of the tumors showing a G to A transition at the second position in codon 12 of the Ha-ras oncogene. Benzo[a]pyrene-induced skin tumors contain A to T transformation in the second codon of the Ha-ras gene.

iii) Radiation Mutagenesis

The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage and cell killing, generally proportional to the dose rate. Ionizing radiation has been postulated to induce multiple biological effects by direct interaction with DNA, or through the formation of free radical species leading to DNA damage. These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman et al., 1989). Synthesis of cyclin and co-regulated polypeptides is suppressed by ionizing radiation in rat REF52 cells, but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte, et al., 1989).

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art.

In a certain embodiments, an effective expression inducing amount is from about 2 to about 30 Gray (Gy) administered at a rate of from about 0.5 to about 2 Gy/minute. Even more preferably, an effective expression inducing amount of ionizing radiation is from about 5 to about 15 Gy. In other embodiments, doses of 2-9 Gy are used in single doses. An effective dose of ionizing radiation may be from 10 to 100 Gy, with 15 to 75 Gy being preferred, and 20 to 50 Gy being more preferred.

Any suitable means for delivering radiation to a tissue may be employed in the present invention in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

iv) In Vitro Scanning Mutagenesis

Random mutagenesis also may be introduced using error prone PCR (Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In recent years, techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

v) Random Mutagenesis by Fragmentation and Reassmbly

A method for generating libraries of displayed polypeptides is described in U.S. Pat. No. 5,380,721. The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

b. Site-Directed Mutagenesis

Structure-guided site-specific mutagenesis represents a powerful tool for the dissection and engineering of protein-ligand interactions. The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Zeng et al., 1996; Yelton et al., 1995; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

B. PROTEIN EXPRESSION

1. Vectors

Once the soluble protein, polypeptide or peptide encoding sequence(s) and alpha complementing protein, polypeptide or peptide encoding sequence(s) are selected, they may be operatively expressed in a recombinant vector. The expression may be in vivo or in vitro, to assay the refolding and complementation process. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Tables 1 lists several elements/promoters that may be employed, in the context of the present invention, to regulate the expression of a gene. This list is not intended to be exhaustive of all the possible elements involved in the promotion of expression but, merely, to be exemplary thereof. Table 2 provides examples of inducible elements, which are regions of a nucleic acid sequence that can be activated in response to a specific stimulus.

TABLE 1

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al., 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |

TABLE 1-continued

Promoter and/or Enhancer

| Promoter/Enhancer | References |
| --- | --- |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al, 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), DIA dopamine receptor gene (Lee, et al., 1997), insulin-like growth factor II (Wu et al., 1997), human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

e. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

f. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

g. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

2. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Prokaryotes include gram negative or positive cells. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5 α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include *C. elegans*, HeLa, NIH3T3, Jurkat, 293, Cos, CHO, Saos, yeast, nematodes, insect cells, and $PCl_2$. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

3. Expression Systems

Turning to the expression of the proteins of the present invention, once a suitable nucleic acid encoding sequence has been obtained, one may proceed to prepare an expression system. The engineering of DNA segment(s) for expression in a prokaryotic or eukaryotic system may be performed by techniques generally known to those of skill in recombinant expression.

It is believed that virtually any expression system may be employed in the expression of the proteins of the present invention. Prokaryote- and/or eukaryote-based systems can be employed for use with the present invention to produce nucleic acid sequences, or their cognate polypeptides, proteins and peptides. Many such systems are commercially and widely available.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

It is contemplated that proteins, polypeptides or peptides may be co-expressed with other selected proteins, polypeptides or peptides, wherein the proteins may be co-expressed in the same cell or gene(s) may be provided to a cell that already has another selected protein. Co-expression may be achieved by co-transfecting the cell with two distinct recombinant vectors, each bearing a copy of either of the respective DNA. Alternatively, a single recombinant vector may be constructed to include the coding regions for both of the proteins, which could then be expressed in cells transfected with the single vector. In either event, the term "co-expression" herein refers to the expression of both at least one selected nucleic acid or gene encoding one or more proteins, polypeptides or peptides and at least a second selected nucleic acid or gene encoding at least one or more secondary selected proteins, polypeptides or peptides in the same recombinant cell.

It is contemplated that proteins may be expressed in cell systems or grown in media that enhance protein production. One such system is described in U.S. Pat. No. 5,834,249, incorporated herein by reference. In certain embodiments, the fusion protein may be co-expressed with one or more proteins that enhance refolding. Such proteins that enhance refolding include, for example, DsbA or DsbC proteins. A cell system co-expressing the DsbA or DsbC proteins are described in U.S. Pat. No. 5,639,635, incorporated herein by reference. In certain embodiments, it is contemplated that a temperature sensitive expression vector may be used to aid assaying protein folding at lower or higher temperatures than many *E. coli* cell strain's optimum growth at about 37° C. For example, a temperature sensitive expression vectors and host cells that express proteins at or below 20° C. is described in U.S. Pat. Nos. 5,654,169 and 5,726,039, each incorporated herein by reference.

As used herein, the terms "engineered" and "recombinant" cells or host cells are intended to refer to a cell into which an exogenous DNA segment or gene, such as a cDNA or gene encoding at least one protein, polypeptide or peptide has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

a. Prokaryotic Expression

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media, for example, LB. The expression of the recombinant protein may be induced, e.g., by adding IPTG to the media or by switching incubation to a higher temperature. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation which more closely resembles that of the native protein. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns.

b. Eukaryotic Expression

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more p rote in, polypeptide or peptide coding sequences.

For expression in *Saccharomyces*, the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In a useful insect system, *Autograph californica* nuclear polyhedrosis virus (AcNPV) is used as a vector to express foreign genes. The virus grows in *Spodoptera frugiperda* cells. The protein, polypeptide or peptide coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, Smith, incorporated herein by reference).

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein.

Different host cells have characteristic and specific mechanisms for the post-translational processing and modification of proteins. Appropriate cells lines or host systems can be chosen to ensure the correct modification and processing of the foreign protein expressed.

Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g. the adenovirus late promoter; the vaccinia virus 7.5K promoter). Further, it is also possible, and may be desirable, to utilize promoter or control sequences normally associated with the gene sequence(s), provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1, E3, or E4) will result in a recombinant virus that is viable and capable of expressing proteins, polypeptides or peptides in infected hosts.

Specific initiation signals may also be required for efficient translation of protein, polypeptide or peptide coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements and transcription terminators.

In eukaryotic expression, one will also typically desire to incorporate into the transcriptional unit an appropriate polyadenylation site (e.g. 5'-AATAAA-3') if one was not contained within the original cloned segment. Typically, the poly A addition site is placed about 30 to 2000 nucleotides "downstream" of the termination site of the protein at a position prior to transcription termination.

C. GENE DELIVERY

The general approach to the aspects of the present invention is to provide a cell with nucleic acid encoding a fusion protein, polypeptide or peptide and/or a nucleic acid encoding a protein, polypeptide or peptide whose activity may be altered by complementation with the fusion protein, thereby permitting a detectable change in the activity of the proteins to take effect. While it is conceivable that the protein(s) may be delivered directly, a preferred embodiment involves providing a nucleic acid encoding the protein(s), polypeptide(s) or peptide(s) to the cell. Following this provision, the polypeptide(s) are synthesized by the transcriptional and translational machinery of the cell, as well as any that may be provided by the expression construct.

In certain embodiments of the invention, the nucleic acid encoding the gene may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

1. DNA Delivery Using Viral Vectors

The ability of certain viruses to infect cells or enter cells via receptor-mediated endocytosis, and to integrate into host cell genome and express viral genes stably and efficiently have made them attractive candidates for the transfer of foreign genes into mammalian cells. Preferred vectors of the present invention will generally be viral vectors.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

a. Adenoviral Vectors

A particular method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein.

The expression vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (E1A and E1B; Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). Recently, adenoviral vectors comprising deletions in the E4 region have been described (U.S. Pat. No. 5,670,488, incorporated herein by reference).

In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recombinant adenovirus and adeno-associated virus (see below) can both infect and transduce non-dividing human primary cells.

b. AAV Vectors

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

c. Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

d. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In certain further embodiments, the vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

e. Modified Viruses

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Other Methods of DNA Delivery

In various embodiments of the invention, DNA is delivered to a cell as an expression construct. In order to effect expression of a gene construct, the expression construct must be delivered into a cell. As described herein, the preferred mechanism for delivery is via viral infection, where the expression construct is encapsidated in an infectious viral particle. However, several non-viral methods for the transfer of expression constructs into cells also are contemplated by the present invention. In one embodiment of the present invention, the expression construct may consist only of naked recombinant DNA or plasmids. Transfer of the construct may be performed by any of the methods mentioned which physically or chemically permeabilize the cell membrane. Some of these techniques may be successfully adapted for in vivo or ex vivo use, as discussed below.

a. Liposome-Mediated Transfection

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

b. Electroporation

In certain embodiments of the present invention, the expression construct is introduced into the cell via electroporation. Electroporation involves the exposure of a suspension of cells and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

c. Calcium Phosphate or DEAE-Dextran

In other embodiments of the present invention, the expression construct is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

d. Particle Bombardment

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

e. Direct Microinjection or Sonication Loading

Further embodiments of the present invention include the introduction of the expression construct by direct microinjection or sonication loading. Direct microinjection has been used to introduce nucleic acid constructs into Xenopus oocytes (Harland and Weintraub, 1985), and LTK$^-$ fibroblasts have been transfected with the thymidine kinase gene by sonication loading (Fechheimer et al., 1987).

f. Adenoviral Assisted Transfection

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

g. Receptor Mediated Transfection

Still further expression constructs that may be employed to deliver nucleic acid construct to target cells are receptor-mediated delivery vehicles. These take advantage of the selective uptake of macromolecules by receptor-mediated endocytosis that will be occurring in the target cells. In view of the cell type-specific distribution of various receptors, this delivery method adds another degree of specificity to the present invention. Specific delivery in the context of another mammalian cell type is described by Wu and Wu (1993; incorporated herein by reference).

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. In certain aspects of the present invention, the ligand will be chosen to correspond to a receptor specifically expressed on the EOE target cell population.

In other embodiments, the DNA delivery vehicle component of a cell-specific gene targeting vehicle may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding. For example, Nicolau et al. (1987) employed lactosyl-ceramide, a galactose-terminal asialganglioside, incorporated into liposomes and observed an increase in the uptake of the insulin gene by hepatocytes. It is contemplated that the tissue-specific transforming constructs of the present invention can be specifically delivered into the target cells in a similar manner.

h. Homologous Recombination

Homologous recombination (Koller and Smithies, 1992) allows the precise modification of existing genes, overcomes the problems of positional effects and insertional inactivation, and allows the inactivation of specific genes, as well as the replacement of one gene for another. Methods for homologous recombination are described in U.S. Pat. No. 5,614,396, incorporated herein in its entirety by reference.

Thus a preferred method for the delivery of transgenic constructs involves the use of homologous recombination. Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, a site for integration is selected within the host cell. Sequences homologous to the integration site are then included in a genetic construct, flanking the selected gene to be integrated into the genome. Flanking, in this context, simply means that target homologous sequences are located both upstream (5') and downstream (3') of the selected gene. These sequences should correspond to some sequences upstream and downstream of the target gene. The construct is then introduced into the cell, thus permitting recombination between the cellular sequences and the construct.

As a practical matter, the genetic construct will normally act as far more than a vehicle to insert the gene into the genome. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, this technique may be used to "knock-out" (delete) or interrupt a particular gene. Thus, another approach for altering or mutating a gene involves the use of homologous recombination, or "knock-out technology". This is accomplished by including a mutated or vastly deleted form of the heterologous gene between the flanking regions within the construct. The arrangement of a construct to effect homologous recombination might be as follows:

. . . vector•5'-flanking sequence•selected gene•selectable marker gene•flanking sequence-3'•vector . . .

Thus, using this kind of construct, it is possible, in a single recombinatorial event, to (i) "knock out" an endogenous gene, (ii) provide a selectable marker for identifying such an event and (iii) introduce a transgene for expression.

Another refinement of the homologous recombination approach involves the use of a "negative" selectable marker. One example is the use of the cytosine deaminase gene in a negative selection method as described in U.S. Pat. No. 5,624,830. The negative selection marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

3. Marker Genes

In certain aspects of the present invention, specific cells are tagged with specific genetic markers to provide information about the fate of the tagged cells. Therefore, the present invention also provides recombinant candidate screening and selection methods which are based upon whole cell assays and which, preferably, employ a reporter gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fluorometric, radioisotopic or spectrophotometric analysis of the cell culture.

In other aspects of the present invention, a genetic marker is provided which is detectable by standard genetic analysis techniques, such as DNA amplification by PCR™ or hybridization using fluorometric, radioisotopic or spectrophotometric probes.

a. Screening

Exemplary enzymes include esterases, phosphatases, proteases (tissue plasminogen activator or urokinase) and other enzymes capable of being detected by their activity, as will be known to those skilled in the art. Contemplated for use in the present invention is green fluorescent protein (GFP) as a marker for transgene expression (Chalfie et al., 1994). The use of GFP does not need exogenously added substrates, only irradiation by near UV or blue light, and thus has significant potential for use in monitoring gene expression in living cells.

Other particular examples are the enzyme chloramphenicol acetyltransferase (CAT) which may be employed with a radiolabelled substrate, firefly and bacterial luciferase, and the bacterial enzymes β-galactosidase and β-glucuronidase. Other marker genes within this class are well known to those of skill in the art, and are suitable for use in the present invention.

b. Selection

Another class of reporter genes which confer detectable characteristics on a host cell are those which encode polypeptides, generally enzymes, which render their transformants resistant against toxins. Examples of this class of reporter genes are the neo gene (Colberre-Garapin et al., 1981) which protects host cells against toxic levels of the antibiotic G418, the gene conferring streptomycin resistance (U.S. Pat. No. 4,430,434), the gene conferring hygromycin B resistance (Santerre et al., 1984; U.S. Pat. Nos. 4,727,028, 4,960,704 and 4,559,302), a gene encoding dihydrofolate reductase, which confers resistance to methotrexate (Alt et al., 1978), the enzyme HPRT, along with many others well known in the art (Kaufman, 1990).

D. CULTURE SYSTEM

For long-term, high-yield production of a recombinant protein, polypeptide or peptide, stable expression is preferred. For example, cell lines that stably express constructs encoding a protein, polypeptide or peptide may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (tk), hypoxanthine-guanine phosphoribosyltransferase (hgprt) and adenine phosphoribosyltransferase (aprt) genes, in tk$^-$, hgprt$^-$ or aprt$^-$ cells, respectively. Also, antimetabolite resistance can be used as the basis of selection for dihydrofolate reductase (dhfr), that confers resistance to methotrexate; gpt, that confers resistance to mycophenolic acid; neomycin (neo), that confers resistance to the aminoglycoside G-418; and hygromycin (hygro), that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the proteins, polypeptides or peptides of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

E. COMPLEMENTATION

The terms "structural complementation", "complementation" or "alpha complementation" as used herein certain embodiments refers to the ability of at least one polypeptide comprising a protein fragment or domain to alter the activity of at least a second polypeptide comprising a protein fragment or domain. In certain embodiments, the at least one polypeptide and the at least second polypeptide are derived from the same precursor protein sequence. A non-limiting example of this is the complementation of β-lactosidase's activity that occurs when the α-fragment and the ω fragment of β-lactosidase interact to produce an active β-lactosidase enzymatic complex.

Other complementing protein fragments are known in the art. Non-limiting examples include the *P. falciparum* thymidylate synthase and dihydrofolate reductase domains (Shallom et al., 1999), and the alpha and beta subunits of the mitochondrial processing peptidase of different species (Adamec et al., 1999), whose activity was detected by the used of temperature sensitive mutant yeast strains.

Thus, it is contemplated that various peptide or polypeptide sequences may be used to produce fusion proteins with a target protein, so that the folding of the target protein into a soluble form can be detected via the change in activity of the complemented peptide or polypeptide. It is also contemplated that additional complementing fragments of commonly used or well known selectable or screenable markers may be made for use in the present invention. Non-limiting examples of such markers include a target binding protein, such as ubiquitin; an enzyme, such as β-galactosidase, cytochrome c, chymotrypsin inhibitor, Rnase, phosphoglycerate kinase, invertase, staphylococcal nuclease, thioredoxin C, lactose permease, amino acyl TRNA synthase, or dihydrofolate reductase; a protein inhibitor, a fluorophore or a chromophore, such as green fluorescent protein, blue fluorescent protein, yellow fluorescent protein, luciferase or aquorin.

It is contemplated that one or more fragments of such markers may be produced through recombinant technology that is well known to those of skill in the art, to produce an complementation system for assaying protein folding as described herein. In a non-limiting example, a nucleic acid encoding a N-terminal sequence of about 250 amino acids or less of a marker protein may be operatively associated with a nucleic acid of a protein of interest to be folded into soluble form. Such nucleic acids may be used to construct an expression vector as described herein, and used to complement a cell that expresses the C-terminal terminal sequence of the marker protein. In an alternative non-limiting example, a nucleic acid encoding a C-terminal sequence of about 250 amino acids or less of a marker protein may be operatively associated with a nucleic acid of a protein of interest to be folded into soluble form. Such nucleic acids may be used to construct an expression vector as described herein, and used to complement a cell that expresses the N-terminal terminal sequence of the marker protein. Of course, one of skill in the art may design nucleic acids encoding marker gene fragments of various lengths. In certain embodiments, the marker gene fragment may encode a polypeptide or peptide of less than about 200, about 150, about 100, about 99, about 98, about 97, about 96, about 95, about 94, about 93, about 92, about 91, about 90, about 89, about 88, about 87, about 86, about 85, about 84, about 83, about 82, about 81, about 80, about 79, about 78, about 77, about 76, about 75, about 74, about 73, about 72, about 71, about 70, about 69, about 68, about 67, about 66, about 65, about 64, about 63, about 62, about 61, about 60, about 59, about 58, about 57, about 56, about 55, about 54, about 53, about 52, about 51, about 50, about 49, about 48, about 47, about 46, about 45, about 44, about 43, about 42, about 41, about 40, about 39, about 38, about 37, about 36, about 35, about 34, about 33, about 32, about 31, about 30, about 29, about 28, about 27, about 26, about 25, about 24, about 23, about 22, about 21, about 20, about 19, about 18, about 17, about 16, about 15, about 14, about 13, about 12, about 11, about 10, about 9, about 8, about 7, about 6, about 5, to about 4 amino acids, which is operatively associated with the nucleic acid encoding the protein that is soluble when folded correctly.

F. SCREENING ASSAYS

The present invention is directed to the use of an α-complementation system to screen for various aspects of protein fold and/or solubility. As discussed above, an important aspect of the invention is the use of a fusion protein that contains sequences from the protein of interest as well as a portion of a marker protein. The marker protein, in the context of the fusion, is incapable of exhibiting its detectable phenotype. However, when expressed in an environment that also includes the complementing portion of the marker protein, "complementation" takes place and a detectable event occurs, assuming that the protein is properly folded and remains soluble. This assay provides many advantages, including fidelity, sensitivity, ease of handling, and ready adaptability.

1. Methods

There are three primary applications for the invention: screening of proteins for suitability in recombinant polypeptide production, screening for mutants or domain boundaries with altered folding and/or solubility profiles (e.g., diagnosis of disease), and screening for drugs that modulate protein folding and/or solubility. In the first embodiment, the method includes the steps of:
  a) providing an expression construct comprising (i) a gene encoding a fusion protein, said fusion protein comprising a protein of interest fused to a first segment of a marker protein, wherein said first segment does not affect the folding or solubility of the protein of interest, or affects it only is a systematic (i.e., predictable and repeatable) manner and (ii) a promoter active in said host cell and operably linked to said gene;
  b) expressing said fusion protein in a host cell that also expresses a second segment of said marker protein, wherein said second segment is capable of structural complementation with said first segment; and
  c) determining structural complementation.

By comparing the degree of structural complementation in the method with that seen with appropriate negative controls, changes in folding and/or solubility of said protein can be determined. By looking at particular cell types from patients suspected of having particular disease states, this general method of screening can be transformed into a specific diagnostic method.

In another embodiment, a method of screening for folding and/or solubility mutants is provided, and includes the steps of:
  a) providing a gene encoding fusion protein comprising (i) a protein of interest and (ii) a first segment of a marker protein, wherein said first segment does not affect the folding or solubility of the protein of interest, or affects it only is a systematic (i.e., predictable and repeatable) manner, wherein said fusion protein is not properly folded and/or soluble when expressed in said host cell;
  b) mutagenizing that portion of the gene encoding said protein of interest;
  c) expressing said fusion protein in a host cell that expresses a second segment of said marker protein, wherein said second segment is capable of structural complementation with said first segment; and
  d) determining structural complementation.

Again, a relative change in structural complementation, as compared to the structural complementation observed with the unmutagenized fusion protein, indicates a change in proper folding and/or solubility of said protein. An alternative embodiment involves the mutation of a gene of interest prior to its fusion with the marker protein segment.

Finally, a third assay involves screening for candidate modulator substances that modulate protein folding and/or solubility, including the steps of:
  a) providing an expression construct comprising (i) a gene encoding fusion protein, said fusion protein comprising a protein of interest fused to a first segment of a marker protein, wherein said first segment does not affect the folding or solubility of the protein of interest, or affects it only is a systematic (i.e., predictable and repeatable) manner, and (ii) a promoter active in said host cell and operably linked to said gene;
  b) expressing said fusion protein in a host cell that expresses a second segment of said marker protein, wherein said second segment is capable of structural complementation with said first segment;
  c) contacting the host cell with said candidate modulator substance; and
  d) determining structural complementation.

Again, a relative change in structural complementation, as compared to the structural complementation observed in the absence of said candidate modulator substance, indicates that said candidate modulator substance is a modulator of protein folding and/or solubility 2. Modulators As used herein the term "candidate substance" refers to any molecule that may potentially inhibit or enhance protein folding and/or solubility. The candidate substance may be a protein or fragment thereof, a small molecule, or even a nucleic acid molecule. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

3. Assay Formats

A quick, inexpensive and easy assay to run is an in vitro assay. Various cell lines can be utilized for such screening assays, including cells specifically engineered for this purpose, as discussed in detail above. Depending on the assay, culture may be required. The cell is examined using α-complementation as a readout. Alternatively, molecular analysis may be performed, for example, looking at protein expression, mRNA expression (including differential display of whole cell or polyA RNA) and others.

In vivo assays involve the use of various animal models, including transgenic animals that have been engineered to express both the fusion protein (target protein+first marker segment) and the complementing molecule (second marker segment). Due to their size, ease of handling, and information on their physiology and genetic make-up, mice are a preferred embodiment, especially for transgenics. However, other animals are suitable as well, including insects, nematodes, rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter protein folding and/or solubility, as compared to a similar animal not treated with the candidate substance(s), identifies a modulator.

Treatment of these animals with candidate substances will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

4. High Throughput and Flow Cytometry

High throughput formats are of particular use in drug screening. Flow cytometry involves the separation of cells or other particles in a liquid sample based upon signals generated in the host cells. Generally, the purpose of flow cytometry is to analyze the separated particles for one or more characteristics thereof. The basis steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparati permit quantitative multiparameter analysis of cellular properties at rates of several thousand cells per second. These instruments provide the ability to differentiate among cell types. Data are often displayed in one-dimensional (histogram) or two dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364 (incorporated by reference), an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent tagged antibodies, which are used to mark one or more cell types for separation.

Other methods for flow cytometry can be found in U.S. Pat. Nos. 4,284,412; 4,989,977; 4,498,766; 5,478,722; 4,857,451; 4,774,189; 4,767,206; 4,714,682; 5,160,974; and 4,661,913, all of which are incorporated by reference.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Antibodies, Chemicals and Expression Vectors

Monoclonal mouse anti-HA and polyclonal sheep anti-MBP antibodies were purchased from BabCO (Richmond, Calif.). Horseradish peroxidase-conjugated (HRP) secondary antibodies were from Jackson ImmunoResearch Laboratories (West Grove, Pa.). Isopropyl-β-D-thiogalactopyranoside (IPTG) and 5-bromo-4-chloro-3-indolyl-β-D-galactopyranoside (X-gal) were from Boehringer Mannheim (Indianapolis, Ind.). O-nitrophenyl-β-D-galactopyranoside (ONPG) was purchased from Sigma (St. Louis, Mo.). The expression vector pMAL-c2x, coding for an MBP-α fusion, was from New England Biolabs (Beverly, Mass.). A plasmid containing cDNA for the LivF protein of *M. jannaschii* (MJ1267) was obtained from the American Type Culture Collection. Plasmid pAPP770 containing cDNA for the Alzheimer's precursor protein (APP) was the generous gift of Dr. J. Herz, Dept. Molecular Genetics, UT Southwestern, Dallas, Tex. Plasmid pTRx.parallel1 containing cDNA for thioredoxin was the generous gift of Dr. K. Gardner, Dept. Biochemistry, UT Southwestern, Dallas, Tex. Plasmid pGex-2t containing cDNA for glutathione S-transferase was from Amersham/Pharmacia (Piscataway, N.J.).

Construction of α-Fusion Expression Vectors

Complementary DNA fragments coding for residues 404-644 (NBD1-B) and 419-655 (NBD1-D) of CFTR were excised using NdeI and XhoI from pET28a expression plasmids generated as previously described (Qu & Thomas, 1996). Based upon homology to the recently published H is P NBD crystal structure (Hung et al., 1998), these constructs are predicted to contain the entire first NBD of CFTR. The resulting fragments were ligated into NdeI/SalI-digested pMal-c2x in place of the maltose-binding protein (MBP), forming an in-frame fusion with the α-fragment (residues 7-58 from full length β-galactosidase). Expression cassette PCR was used to assmble the other α-fusion constructs examined. The MJ1267 cDNA was also subcloned into the NdeI and SalI sites of pMal-c2x. The resulting vector contained an in-frame stop codon between MJ1267 and the polylinker of pMAL-c2x which was removed by site-directed mutagenesis completing the α-fusion construct. TRx, GST and Aβ (APP residues 1-42) were each ligated into NdeI/SacI-digested pMal-c2x. The cloning strategy used to assemble the tandem Aβ/α-fusion construct, Aβ-rpt, was similar to that described elsewhere (Culvenor et al., 1998), and utilized an internal EcoRI site to generate an exact Aβ(1-42) repeat with no intervening sequence. All targets were subcloned in the pMal-c2x vector and, therefore, utilize the same promoter. In addition, the ABC transporter NBDs evaluated were also expressed in BL21 cells under the control of the T7 promoter of pET28a. In each case, fidelity of PCR™ products and constructs was verified by restriction mapping and DNA sequencing.

To serve as a marker for some of the expressed proteins (MJ1267, CFTR-NBD1, TRx, GST and Aβ), an HA-tag sequence was introduced into the SalI site of the pMal-c2x expression vector using two annealed complimentary oligonucleotides coding for the tag sequence and flanked by SalI linker sequences. Correct orientation of the resulting ligation products was confirmed by DNA sequencing.

Site-Directed Mutagenesis

Oligonucleotide-directed mutagenesis using the Quick-Change mutagenesis kit (Stratagene, La Jolla, Calif.) was performed to generate the mutant MBP proteins in the expression vector pMal-c2x. The sequences of the antisense mutagenic primers used are as follows:

G32D/I33P-
5'-GATGCTCAACGGTGACTTTAGGATCGGTATCTTCTCGAATTTC-3'

G32D-
5'-CAACGGTGACTTTAATATCGGTATCTTTCTCG-3'

I33P-
5'-GGTGACTTTAGGTCCGGTATCTTTCTCG-3'

Mutation incorporation was verified by DNA sequencing. Plasmid DNA was purified using reagents supplied by Qiagen Inc.

Expression of Fusion Proteins

Expression constructs were transformed into DH5α *E. coli* by standard methods and colonies selected on LB-agar plates supplemented with 100 μg/mL ampicillin (amp). From single colonies, 10 mL LB+amp cultures were inoculated and allowed to grow overnight at 37° C. The following day, the overnight culture was diluted 1000-fold into a fresh 10 mL LB+amp culture and allowed to grow to mid log phase ($OD_{600}$~0.5). Protein production was induced by the addition of IPTG to 0.3 mM and the cells were further incubated for the indicated times.

In Vitro Assay of β-Gal Complementation

After the completion of fusion protein expression, cells (1.5 mL) were harvested by centrifugation at 10,000×g for two minutes. After removal of the supernatants, the cell pellets were resuspended in 1 mL of buffer Z (10 mM KCl, 2.0 mM MgSO4, 100 mM NaHP04, pH 7.0). The cells were pelleted again, resuspended in 0.3 mL buffer Z and lysed by three freeze/thaw cycles between liquid nitrogen and a 37° C. water bath. Next, 0.1 mL of the resulting cell lysate was transferred to a clean microfuge tube to which buffer Z (0.7 ml) supplemented with 0.27% β-mercaptoethanol was added. Reactions were initiated by the addition of 160 µL of ONPG solution (4.0 mg/mL dissolved in buffer Z) and incubated at 37° C. for 10 min. Reactions were quenched by the addition of 0.4 mL 1 M $Na_2CO_3$. Tubes were then centrifuged at 10,000×g for 10 min to remove debris and the supernatant's absorption at 420 nm was measured.

Analysis of Soluble and Insoluble Fractions

To biochemically analyze the solubility characteristics of the expressed fusion proteins, 3 mL of culture from cells induced for the indicated times was harvested by centrifugation, washed once and resuspended in 600 µL lysis solution (100 mM NaCl, 1 mM EDTA, 50 mM Tris Cl, pH 7.6). The cell suspensions were lysed by sonication three times for 30 sec at 50° C. duty cycle and power output of 4 using a Branson model 450 sonifier fit with a microtip probe. All manipulations were carried out on ice. After sonication, the solution was centrifuged to separate soluble and insoluble fractions at 10,000×g in a microfuge at 4° C. for 10 min. Supernatant and pellet fractions were analyzed by SDS PAGE and Western blotting where appropriate.

SDS PAGE and Western Blotting

Expressed proteins were analyzed by electrophoresis through 10% Tricine-SDS polyacrylamide gels using the buffer system of Schagger and von Jagow (1987). Protein bands were visualized by staining with coomassie blue. For Western immunoblotting, standard methods were employed for transfer of proteins from gels to nitrocellulose. Resulting membranes were blocked in TBS containing Tween-20 and 10% dehydrated milk for at least 1 hr and incubated at room temperature with the indicated primary antibodies. Immunoreactive bands were visualized by ECL (Amersham, Piscataway, N.J.) using appropriate HRP-conjugated secondary antibodies and X-ray film. The density of bands on coomassie stained gels and exposed x-ray film were measured on an Agfa Arcus scanner and quantified using Molecular Analyst software (BioRad, Hercules, Calif.).

Blue/White Screening for β-Gal Complementation

Single colonies of DH5α containing the individual expression constructs were analyzed for the ability of the α-fusion proteins to complement β-gal activity in vivo. Bacteria harboring each construct were streaked to single colonies on LB-agar plates supplemented with 100 µg/mL ampicillin, 80 µg/mL Xgal, and 0.1 mM IPTG. The plates were incubated at 37° C. for 18 to 48 hr and activity of β-gal was assessed by visualization of blue color in α-complementing colonies.

Colorimetric Screening for β-Gal Complementation in 96-Well Plates

Cells harboring each of the indicated expression constructs were grown to mid log phase ($OD_{600} \approx 0.5$) from overnight cultures as described above. 125 µl of each culture ws transferred to individual wells of a flat-bottom 96-well plate containing 125 µl LB media supplemented with 100 µg/mL ampicillin and 0.6 mM IPTG (resulting in a final [IPTG] of 0.3 mM). The plates were then placed on an orbit shaker at 37° C. with rapid shaking. After induction for 1 hr, X-gal was added to a final concentration of 80 µg/mL, and the plate was returned to the shaker at 37° C. overnight.

Example 2

Results

Figure 1B:
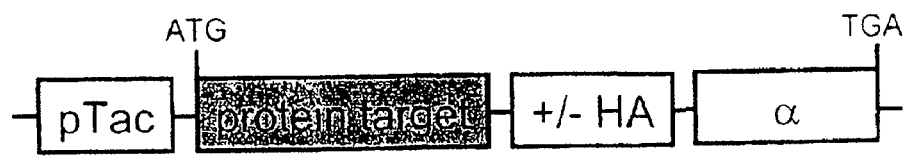

In order to test the ability of α-fragment chimeras to complement the ω-fragment of β-gal and report target protein solubility by producting active β-gal, model polypeptides were fused to the N-terminus of the α-fragment in an inducible bacterial expression plasmid (FIG. 1B). Initial experiments focused on the maltose binding protein (MBP) of E. coli. MBP is normally secreted into the periplasm of E. coli, however, the construct used in the present study lacks the required leader sequence and therefore, folds in the cytoplasm where the ω-fragment is located.

To assess the relative abilities of the expressed α-fusion proteins to complement β-gal activity in vivo, E. coli harboring the fusion expression constructs were plated on IPTG/X-gal indicator plates and the development of blue color in resulting colonies was monitored. pUC19-transformed DH5α E. coli, which express a 54 residue α-fragment (residues 6-59 of β-gal), are the most intensely blue. This represents the level of β-gal complementation attributable to the α-fragment alone. The MBP-α fusion protein (MBP residues 1-366, α: residues 7-58 of β-gal) also yields significant α-complementation, although less than observed for pUC19. Yanisch-Perron et al. (1985).

Previously, several mutations were identified which lead to diminished solubility and reduced periplasmic yield of MBP (Betton Hofnung, 1986). For example, mutation of two residues, 133P and G32D, decreased soluble periplasmic MBP by more than 100-fold. This double mutation was introduced into MBP/a fusion construct, and monitored for α-complemenation on indicator plates. The wild-type MPB and the double mutant expressed at equivalent levels. Consistent with the previously reported effect of these mutations on the in vivo solubility of MBP, the G32D/I33P double mutation significantly impaired the solubility and, thus, ability of the fusion protein to complement β-gal activity on indicator plates.

To test the generality of the assay system, a series of α-fusion constructs were generated. Fusion to α of either TRx or GST (two highly soluble proteins used regularly as fusions to aid in the solubility of ill-behaved partners) and express in DH5α on indicator plates results in blue color development that is as intense as that observed for the MBP/α fusion construct. Next, a series of nucleotide binding domains (NBD) from two ATP binding-cassette (ABC) transporters were generated and examined. Two are polypeptides predicted to include the first NBD of the cystic fibrosis transmembrane conductance regulator (CFTR): NBD1-B (CFTR residues 404-644), and NBD1-D (CFTR residues 419-655). This domain has poor solubility properties due either to inherently limited solubility in the absence of other domains of the protein with which it normally interacts, or to marginal stability/misfolding or both. Several mutations within this domain prevent proper folding of the full length CFTR in vivo and, thus, lead to cystic fibrosis. The third NBD, LivF (MJ1267), is a subunit of the branched chain amino acid transporter from the hyperthermophilic archaeon M. jannaschi. CFTR NBD1 has been shown to be insoluble, forming inclusion bodies when expressed in E. coli (Qu & Thomas, 1996), unless fused to soluble protein such as wild-type MBP (Ko et al., 1993) or GST (King & Sorscher, 1998). MJ1267, however, has proven much more soluble, yielding 10% soluble protein from a T7 expression system in BL21 E. coli.

When expressed in DH5α on indicator plates, both CFTR NBD/α fusions result in very little blue color, even after 48 hr of growth although the NBD1-D/α fusion appears to complement measurably more than NBD1-B. By contrast, expression of the MJ1267/α fusion results in a significantly elevated level of blue color when compared to either of the CFTR NBD/α fusion proteins. The MBP/α fusion proteins express at higher levels than the NBD/α fusions as a group, and thus more activity. It should be noted that relative levels of α-complementation, as evidenced by blue color on indicator plates, can be observed at the single colony level for each of the constructs tested, providing a measure that is independent of plated cell density.

To test whether the α-complementation assay is adaptable to a format amenable to rapid-throughput screening, the constructs described above were analyzed for the development of blue color in a 96-well plate β-gal assay. The levels of blue color obtained in the micro titer plate assay for each construct agrees well with that obtained in the agar plate assay. In fact, the difference in color levels observed upon comparison of the two CFTR-NBD/α-fusions is more apparent in the 96-well plate assay.

To verify the hypothesis that the intensity of blue color on indicator plates is reporting target protein solubility, the amount of soluble versus insoluble protein was measured in biochemical fractionation experiments. E. coli expressing wild-type, G32D, I33P, and G32D/I33P-MBP/α fusions were subjected to cell disruption and fractionation by centrifugation. Analysis by SDS PAGE of the soluble and insoluble fractions for each fusion protein revealed a correlation between solubility and level of blue color on Xgal plates. It is important to note that the aga plate β-gall assay, after long incubation times, is most sensitive to changes from insoluble to higher levels of solubility, the range of greatest practical utility. The wild-type MBP/α fusion fractionates primarily to the supernatant, while the double mutant (G32D/I33P) fractionates primarily to the pellet. Fractionation results were further confirmed by Western blots probed with anti-MBP antibodies. The fraction of MBP/a fusions that are soluble is in agreement with the previously published stability and folding yield of these mutants without the α-fragment marker (Betton & Hofnung, 1996). This suggests that the α-fragment does not significantly impact the overall solubility characteristics of the MBP fusion proteins and is therefore a good reporter of target protein solubility. Similarly, the high levels of blue color observed for the GST/α and TRx/α fusions correlates well with the biochemical fractionation experiments, which indicate a majority of both of these proteins partions to the soluble fraction.

A correlation between the biochemical solubility and α-complementation (as indicated by blue color of colonies in the plate assays) also was demonstrated for the NBD/α fusion constructs. Both CFTR NBD/α fusion proteins exhibit little to no blue color, and virtually all of the fusion protein partitions to the insoluble fraction whether expressed with (DH5α expression) or without (BL21 expression) the α-fragment. In contrast, MJ1267, when expressed as an α-fragment fusion, produces a significantly higher level of blue color relative to either of the CFTR-NBD/α fusions. This correlates with the partial solubility of MJ1267 either with (DH5α expression) or without (BL21 expression) the α-fragment. Taken together, these results suggest that in these cases, the relatively small α-fragment, when fused to a target polypeptide, does not have large effects on the target's solubility; neither increasing that of the otherwise insoluble targets (CFTR-NBDs), nor decreasing that of the partially soluble one (MJ1267).

A quantitative measure of α-complementation of β-gal by each of the fusion targets was obtained by the direct measurement of activity in cell lysates. A total of four MBP folding variants were utilized to establish the quantitative relationship within a target system between β-gal activity and biochemical solubility. Table 3 summarizes the results of these in vitro enzyme assays.

TABLE 3

| Target Protein | β-gal Activity (units/cell) |
| --- | --- |
| MBP wild-type | 102 ± 19 |
| G32D | 94 ± 21 |
| I33P | 46 ± 12 |
| G32D/I33P | 14 ± 3 |
| GST | 134 ± 8 |
| TRx | 159 ± 14 |
| CFTRNBD1-B | 5 ± 1 |
| CFTRNBD1-D | 6 ± 2 |
| MJ1267 (LivF) | 12 ± 6 |

A unit of β-gall activity is defined as the amount of enzyme required to hydrolyze one μmole of ONPG to o-nitrophenol and D-galactose per minute. Note that the polylinker between MBP (and mutants thereof) and the α-fragment is 36 residues in length. This linker was reduced to 9 residues during construction of the CFTR-, LivF-, GST-, and TRx-α fusion constructs.

Figure 2:
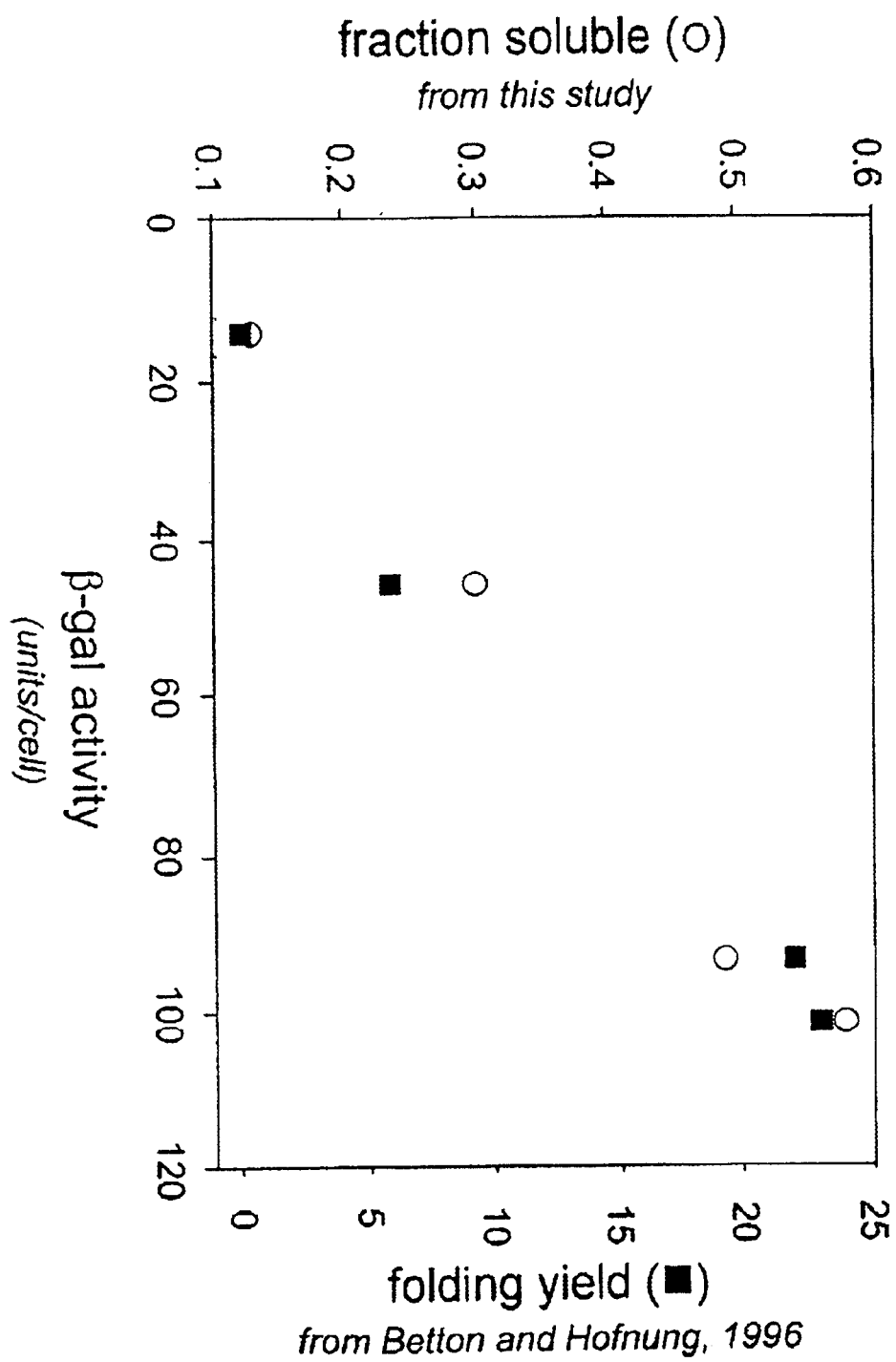
FIG. 2. Correlation of β-galactosidase activity with fusion protein solubility and folding. A scatter plot correlating the in vitro β-galactosidase activity measured in cell lysates (see Table 1) with the fraction soluble (open circles) and the reported periplasmic yield (filed squares) for each of the MBP/α-fragment fusion proteins examined.

Activity correlates well with the relative levels of blue color observed for these constructs. The plate assay is less able to distinguish highly soluble targets from those of intermediate solubility (MBP single mutants) most likely due to integration of the signal during growth of the colonies. FIG. 2 shows a linear relationship between the enzymatic activity (Table 3) and the biochemical soluble fraction for each of the MBP/a fusions as assessed by densitometry of Coomassie-stained gels. Again, the activities show a linear correlation with the periplasmic folding yields for the unfused MBPs reported by Betton and Hofaung (1996), further supporting the assay's ability to report on the intrinsic folding/solubility properties of the target proteins. The differing magnitude of the effects reported here when compared with those previously reported by Betton and Hofnung (1996) may reflect the cellular environments where folding takes place since the present constructs must fold in the cytoplasm.

In addition to cystic fibrosis, many other human diseases are associated with inappropriate folding and/or aggregation of proteins (Thomas et al., 1995; Tan & Pepys, 1994; Wells & Warren, 1998). To test whether the structural complementation assay has application to such proteins, the Alzheimer's Aβ (1-42) peptide, which forms insoluble fibrils in the brains of affected individuals, was selected as an additional test case. When fused to the α-fragment and expressed in E. coli on indicator plates, the fusion protein is unable to efficiently complement β-gal activity, resulting in very little development of blue color. In contrast, mutation of phenylalanine to proline at position 19 of Aβ (F19P), a mutation known to retard fibril formation in vitro (Wood et al., 1995), results in a clear and measurable increase in blue color on indicator plates, approximately a three-fold increase in β-gal activity, and increased fusion protein in the soluble fraction at equivalent levels of expression. Recently, Culvenor and co-workers reported the production of "large intracellular deposits" of Aβ-immunoreactive material upon the expression of Aβ(1-42) as a tandem head-to-tail duplex in yeast (Culvenor et al., 1998). To assess the ability of this assay to report on the solubility state of such a construct, the inventors assembled and expressed a tandem repeat of Aβ as a fusion with the α-fragment (Aβ-rpt). Colonies expressing the Aβ-rpt/α fusion protein exhibit no detectable blue color on indicator plates, in vitro β-gal activity less than that observed for the wild-type Aβ/α a fusion, and no detectable protein is in the soluble fraction. Interestingly, the Aβ-rpt protein aggregates to form a ladder of increasingly higher molecular weight insoluble species, a property absent from the single Aβ/α fusion and perhaps more reflective of the disease condition.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,826,364
U.S. Pat. No. 4,215,051
U.S. Pat. No. 4,284,412
U.S. Pat. No. 4,430,434
U.S. Pat. No. 4,498,766
U.S. Pat. No. 4,559,302
U.S. Pat. No. 4,661,913
U.S. Pat. No. 4,683,202
U.S. Pat. No. 4,714,682
U.S. Pat. No. 4,727,028
U.S. Pat. No. 4,767,206
U.S. Pat. No. 4,774,189
U.S. Pat. No. 4,797,368
U.S. Pat. No. 4,857,451
U.S. Pat. No. 4,879,236
U.S. Pat. No. 4,960,704
U.S. Pat. No. 4,989,977
U.S. Pat. No. 5,139,941
U.S. Pat. No. 5,160,974
U.S. Pat. No. 5,220,007
U.S. Pat. No. 5,221,605
U.S. Pat. No. 5,238,808
U.S. Pat. No. 5,284,760
U.S. Pat. No. 5,354,670
U.S. Pat. No. 5,366,878
U.S. Pat. No. 5,380,721
U.S. Pat. No. 5,389,514
U.S. Pat. No. 5,478,722
U.S. Pat. No. 5,614,396
U.S. Pat. No. 5,624,830
U.S. Pat. No. 5,635,377
U.S. Pat. No. 5,639,635
U.S. Pat. No. 5,654,169
U.S. Pat. No. 5,670,488
U.S. Pat. No. 5,726,039
U.S. Pat. No. 5,789,166
U.S. Pat. No. 5,798,208
U.S. Pat. No. 5,830,650
U.S. Pat. No. 5,834,249
U.S. Pat. No. 5,871,986
U.S. Pat. No. 5,925,565
U.S. Pat. No. 5,928,906
U.S. Pat. No. 5,935,819
U.S. Pat. No. 5,935,824
U.S. Pat. No. 5,990,275
EPO 0273085

Adamec et al., "Complementation between mitochondrial processing peptidase (MPP) subunits from different species", *Arch Biochem Biophys*, 370(1):77-85, 1999.

Almendro, Bellon, Rius, Lastres, Langa, Corbi, Bemabeu, "Cloning of the human platelet endothelial cell adhesion molecule-1 promoter and its tissue-specific expression. Structural and functional characterization," *J. Immunol.*, 157(12):5411-5421, 1996.

Alt et al., *J. Biol. Chem.*, 253:1357, 1978.

Angel et al., "12-0-tetradecanoyl-phorbol-13-acetate Induction of the Human Collagenase Gene is Mediated by an Inducible Enhancer Element Located in the 5' Flanking Region," *Mol. Cell. Biol.*, 7:2256, 1987a.

Angel et al., "Phorbol Ester-Inducible Genes Contain a Common cis Element Recognized by a TPA-Modulated Trans-acting Factor," *Cell*, 49:729, 1987b.

Atchison and Perry, "Tandem Kappa Immunoglobulin Promoters are Equally Active in the Presence of the Kappa Enhancer: Implications for Model of Enhancer Function," *Cell*, 46:253, 1986.

Atchison and Perry, "The Role of the Kappa Enhancer and its Binding Factor NF-kappa B in the Developmental Regulation of Kappa Gene Transcription," *Cell*, 48:121, 1987.

Ausubel et al., In: *Current Protocols in Molecular Biology*, John, Wiley and Sons, Inc., 1994.

Baichwal and Sugden, "Vectors for gene transfer derived from animal DNA viruses: Transient and stable expression of transferred genes," In: Kucherlapati R, ed. Gene transfer. New York: Plenum Press, pp. 117-148, 1986.

Banerji et al., "A lymphocyte-specific cellular enhancer is located downstream of the joining region in immunoglobulin heavy-chain genes," *Cell*, 35:729, 1983.

Banerji et al, "Expression of a Beta-Globin Gene is Enhanced by Remote SV40 DNA Sequences," *Cell*, 27:299, 1981.

Berkhout et al., "Tat trans-activates the human immunodeficiency virus through a nascent RNA target," *Cell*, 59:273, 1989.

Betton, Boscus, Missiakas, Raina, Hofnung, "Probing the structural role of an alpha beta loop of maltose-binding protein by mutagenesis: heat-shock induction by loop variants of the maltose-binding protein that form periplasmic inclusion bodies," *J. Mol. Biol.*, 262(2):140-150, 1996.

Blackburn, Hasnain, Pettingill, Strange, "Copper K-extended x-ray absorption fine structure studies of oxidized and reduced dopamine beta-hydroxylase. Confirmation of a sulfur ligand to copper(I) in the reduced enzyme," *J. Biol. Chem*, 266(34):23120-23127, 1991.

Blackwell and Horgan, "A novel strategy for production of a highly expressed recombinant protein in an active form," *FEBS Lett.*, 295:10-12, 1991.

Blanar et al., "A Gamma-Interferon-Induced Factor That Binds the Interferon Response Sequence of the MHC Class I Gene, H-2 Kb," *EMBO J*, 8:1139, 1989.

Bodine and Ley, "An Enhancer Element Lies 3' to the Human A Gamma Globin Gene," *EMBO J*, 6:2997, 1987.

Boothman, Bouvard, Hughes, "Identification and characterization of X-ray-induced proteins in human cells," *Cancer Res.*, 49(11):2871-2878, 1989.

Borek, "Oncogenes and cellular controls in radiogenic transformation of rodent and human cells," *Carcinog. Compr. Surv.*, 10:303-316, 1985.

Boshart et al., "A very strong enhancer is located upstream of an immediate early gene of human cytomegalovirus," *Cell*, 41:521, 1985.

Bosze et al., "A transcriptional enhancer with specificity for erythroid cells is located in the long terminal repeat of the friend murine leukemia virus," *EMBO J*, 5:1615, 1986.

Bourot et al., "Glycine betaine-assisted protein folding in a lysA mutant of *Escherichia coli.,*". *J. Biol. Chem.*, 275:1050-1056, 2000.

Braddock et al., "HIV-I Tat Activates Presynthesized RNA In the Nucleus," *Cell*, 58:269, 1989.

Brown, Hong-Brown, Welch, "Correcting temperature-sensitive protein folding defects," *J. Clin. Invest.*, 99:1432-1444, 1997.

Bruijn et al., "Aggregation and motor neuron toxicity of an ALS-linked SOD1 mutant independent from wild-type SOD1," *Science*, 281:1851-1853, 1998.

Bulla and Siddiqui, "The hepatitis B virus enhancer modulates transcription of the hepatitis B virus surface-antigen gene from an internal location," *J. Virol.*, 62:1437, 1986.

Burks, Chen, Georgiou, Iverson, "In vitro scanning saturation mutagenesis of an antibody binding pocket, *Proc. Natl. Acad. Sci. U.S.A.*, 94(2):412-417, 1997.

Cadwell and Joyce, "Randomization of genes by PCR mutagenesis," *PCR Methods App.*, (1):28-33, 1992.

Campbell and Villarreal, "Functional analysis of the individual enhancer core sequences of polyoma virus: Cell-specific uncoupling of DNA replication from transcription," *Mol. Cell. Biol.*, 8:1993, 1988.

Campere and Tilghman, "Postnatal repression of the α-fetoprotein gene is enhancer independent," *Genes and Dev.*, 3:537, 1989.

Carbonelli et al. "A plasmid vector for isolation of strong promoters in *E. coli*," *FEMS Microbiol Lett.* 177(1):75-82, 1999.

Celander and Haseltine, "Glucocorticoid regulation of murine leukemia virus transcription elements is specified by determinants within the viral enhancer region," *J. Virology*, 61:269, 1987.

Celander et al., "Regulatory elements within the murine leukemia virus enhancer regions mediate glucocorticoid responsiveness," *J. Virology*, 62:1314, 1988.

Chalfie et al., *Science*, 263:802-805, 1994.

Chandler et al., "DNA sequences bound specifically by glucocorticoid receptor in vitro render a heterlogous promoter hormone responsive in vivo," *Cell*, 33:489, 1983.

Chandler et al., "RNA splicing specificity determined by the coordinated action of RNA recognition motifs in SR proteins," *Proc Natl Acad Sci USA*. 94(8):3596-3601, 1997.

Chang et al., "Foreign gene delivery and expression in hepatocytes using a hepatitis B virus vector," *Hepatology*, 14:134A, 1991.

Chang et al., "Glucose-regulated Protein (GRP94 and GRP78) Genes Share Common Regulatory Domains and are Coordinately Regulated by Common Trans-acting Factors," *Mol. Cell. Biol.*, 9:2153, 1989.

Chatterjee et al., "Negative Regulation of the Thyroid-Stimulating Hormone Alpha Gene by Thyroid Hormone: Receptor Interaction Adjacent to the TATA Box," *Proc. Natl. Acad. Sci. U.S.A.*, 86:9114, 1989.

Chen and Okayama, "High-efficiency transformation of mammalian cells by plasmid DNA," *Mol. Cell. Biol.* 7:2745-2752, 1987

Choi et al., "An Altered Pattern of Cross-Resistance in Multi-Drug-Resistant Human Cells Results From Spontaneous Mutations in the Mdr-1 (P-glycoprotein) Gene," *Cell*, 53:519, 1988.

Clark et al, "Cell lines for the production of recombinant adeno-associated virus," *Human Gene Therapy*, 6:1329-1341, 1995.

Cocea, "Duplication of a region in the multiple cloning site of a plasmid vector to enhance cloning-mediated addition of restriction sites to a DNA fragment," *Biotechniques*, 23:814-816, 1997.

Coffin, "Retroviridae and their replication," In: *Virology*, Fields et al (eds.), New York: Raven Press, pp. 1437-1500, 1990.

Cohen et al, "A Repetitive Sequence Element 3' of the Human c-Ha-ras1 Gene Has Enhancer Activity," *J. Cell. Physiol.*, 5:75, 1987.

Colbere-Garapin, Horodniceanu, Kourilsky, Garapin, "A new dominant hybrid selective marker for higher eukaryotic cells," *J. Mol. Biol*, 150(1):1-14, 1981.

Colon and Kelly, "Partial denaturation of transthyretin is sufficient for amyloid fibril formation in vitro, *Biochemistry*, 31:8654-8660, 1992.

Cooley, Kelley, Spradling, "Insertional mutagenesis of the *Drosophila* genome with single P elements," *Science*, 239 (4844):1121-1128, 1988.

Costa et al., "The cell-specific enhancer of the mouse transthyretin (prealbumin) gene binds a common factor at one site and a liver-specific factor(s) at two other sites," *Mol. Cell. Biol.*, 8:81, 1988.

Cotten et al., "High efficiency receptor-mediated delivery of small and large (48 kilobase) gene constructs using the endosome disruption activity of defective or inactivated adenovirus particles," *Proc. Natl. Acad. Sci. USA*, 89:6094-6098, 1992.

Coupar et al., "A general method for the construction of recombinant vaccinia virus expressing multiple foreign genes," *Gene*, 68:1-10, 1988.

Cripe et al., "Transcriptional Regulation of the Human Papilloma Virus-16 E6-E7 Promoter by a Keratinocyte-Dependent Enhancer, and by Viral E2 Trans-Activator and Repressor Gene Products: Implications for Cervical Carcinogenesis," *EMBO J*, 6:3745, 1987.

Culotta and Hamer, "Fine Mapping of a Mouse Metallothionein Gene Metal-Response Element," *Mol. Cell. Biol.*, 9:1376, 1989.

Culvenor, Henry, Hartmann, Evin, Galatis, Friedhuber, Jayasena, Underwood, Beyreuther, Masters, Cappai, "Subcellular localization of the Alzheimer's disease amyloid precursor protein and derived polypeptides expressed in a recombinant yeast system," *Amyloid*, 5(2):79-89, 1998.

Cunningham and Wells, "High-resolution epitope mapping of hGH-receptor interactions by alanine-scanning mutagenesis," *Science*, 244(4908):1081-1085, 1989.

Curiel, "Gene transfer mediated by adenovirus-polylysine DNA complexes," In: *Viruses in Human Gene Therapy*, J.-M. H. Vos (Ed.), Carolina Academic Press, Durham, N.C., pp. 179-212, 1994.

Dandolo et al., "Regulation of Polyma Virus Transcription in Murine Embryonal Carcinoma Cells," *J. Virology*, 47:55, 1983.

Davies et al., "Formation of neuronal intranuclear inclusions underlies the neurological dysfunction in mice transgenic for the HD mutation," *Cell*, 90:537-548, 1997.

De Villiers et al., "Polyoma Virus DNA Replication Requires an Enhancer," *Nature*, 312:242, 1984.

Deschamps et al., "Identification of a Transcriptional Enhancer Element Upstream From the Proto-Oncogene Fos," *Science*, 230:1174, 1985.

Dobson, "Protein misfolding, evolution and disease," *TIBS* 24:329-332, 1999.

Edbrooke et al., "Identification of cis-Acting Sequences Responsible for Phorbol Ester Induction of Human Serum Amyloid A Gene Expression Via a Nuclear-Factor-κB-like Transcription Factor," *Mol. Cell. Biol.*, 9:1908, 1989.

Edlund et al., "Cell-Specific Expression of the Rat Insulin Gene: Evidence for Role of Two Distinct 5' Flanking Elements," *Science*, 230:912, 1985.

Fechheimer et al., "Transfection of mammalian cells with plasmid DNA by scrape loading and sonication loading," *Proc. Natl. Acad. Sci. USA* 84:8463-8467, 1987

Feng and Holland, "HIV-I Tat Trans-Activation Requires the Loop Sequence Within Tar," *Nature*, 334:6178, 1988.

Firak and Subramanian, "Minimal Transcription Enhancer of Simian Virus 40 is a 74-Base-Pair Sequence that Has Interacting Domains," *Mol. Cell. Biol.*, 6:3667, 1986.

Flotte et al., "An improved system for packaging recombinant adeno-associated virus vectors capable of in vivo transduction," *Gene Therapy*, 2:29-37, 1995.

Flotte et al., "Gene expression from adeno associated virus vector in airway epithelial cells," *Am. J. Respir. Cell Mol. Biol.*, 7:349-356, 1992.

Flotte et al., "Stable in vivo expression of the cystic fibrosis transmembrane conductance regulator with an adeno-associated virus vector," *Proc. Natl. Acad. Sci. USA*, 90:10613-10617, 1993.

Foecking and Hofstetter, "Powerful and Versatile Enhancer-Promoter Unit for Mammalian Expression Vectors," *Gene*, 45:101, 1986.

Foster, Coffey, Morin, Rastinejad, "Pharmacological rescue of mutant p53 conformation and function," *Science*, 286:2507-2510, 1999.

Fraley and Fomari Kaplan, "Entrapment of a bacterial plasmid in phospholipid vesicles:potential for gene transfer," *Proc. Nat'l. Acad. Sci. USA* 76:3348-3352, 1979

Friedmann, "Progress toward human gene therapy," *Science*, 244:1275-1281, 1989.

Fujita et al., "Interferon-Beta Gene Regulation: Tandemly Repeated Sequences of a Synthetic 6-bp Oligomer Function as a Virus-Inducible Enhancer," *Cell*, 49:357, 1987.

Galvin, Uryu, Lee, Trojanowski, "Axon pathology in Parkinson's disease and Lewy body dementia hippocampus contains alpha-, beta-, and gamma-synuclean," *Proc. Natl. Acad. Sci. U.S.A.*, 96:13450-13455, 1999.

Ghosh and Bachhawat, "Targeting of liposomes to hepatocytes," In: Wu G. and C. Wu ed. Liver diseases, targeted diagnosis and therapy using specific receptors and ligands. New York: Marcel Dekker, pp. 87-104, 1991.

Ghosh-Choudhury et al., "Protein IX, a minor component of the human adenovirus capsid, is essential for the packaging of full-length genomes," *EMBO J*, 6:1733-1739, 1987.

Gilles et al., "A Tissue-Specific Transcription Enhancer Element is Lcoated in the Major Intron of a Rearranged Immunoglobulin Heavy-Chain Gene," *Cell*, 33:717, 1983.

Gloss et al., "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J*, 6:3735, 1987.

Godbout et al., "Fine-Structure Mapping of the Three Mouse Alpha-Fetoprotein Gene Enhancers," *Mol. Cell. Biol.*, 8:1169, 1988.

Gomez-Foix et al., "Adenovirus-mediated transfer of the muscle glycogen phosphorylase gene into hepatocytes confers altered regulation of glycogen," *J. Biol. Chem.*, 267:25129-25134, 1992.

Goodbourn and Maniatis, "Overlapping Positive and Negative Regulatory Domains of the Human β-Interferon Gene," *Proc. Natl. Acad. Sci. USA*, 85:1447, 1988.

Goodbourn et al., "The Human Beta-Interferon Gene Enhancer is Under Negative Control," *Cell*, 45:601, 1986.

Gopal, "Gene transfer method for transient gene expression, stable transformation, and cotransformation of suspension cell cultures," *Mol. Cell. Biol.* 5:1188-1190, 1985.

Graham and Prevec, "Adenovirus-based expression vectors and recombinant vaccines," *Biotechnology*, 20:363-390, 1992.

Graham and Prevec, "Manipulation of adenovirus vectors," In: *Gene Transfer and Expression Protocols*, Murray, E. J., ed., Humana, New Jersey, vol. 7, 109-128, 1991.

Graham and Van Der Eb, "A new technique for the assay of infectivity of human adenovirus 5 DNA," *Virology* 52:456-467, 1973.

Graham et al., "Characteristics of a human cell line transformed by DNA from human adenovirus type 5", *J. Gen. Virol.*, 36:59-72, 1977.

Greene et al., "HIV-1, and Normal T-Cell Growth: Transcriptional Strategies and Surprises," *Immunology Today*, 10:272, 1989.

Grosschedl and Baltimore, "Cell-Type Specificity of Immunoglobulin Gene Expression is Regulated by at Least Three DNA Sequence Elements," *Cell*, 41:885, 1985.

Grunhaus and Horwitz, "Adenovirus as cloning vector," *Seminar in Virology*, 3:237-252, 1992.

Harland and Weintraub, "Translation of mRNA injected into *Xenopus* oocytes is specifically inhibited by antisense RNA," *J. Cell Biol.* 101:1094-1099, 1985.

Harper and Lansbury Jr., "Models of amyloid seeding in Alzheimer's disease and scrapie: mechanistic truths and physiological consequences of the time-dependent solubility of amyloid proteins," *Annu. Rev. Biochem.*, 66:385-407, 1997.

Haslinger and Karin, "Upstream Promoter Element of the Human Metallothionein-II Gene Can Act Like an Enhancer Element," *Proc. Natl. Acad. Sci. U.S.A.*, 82:8572, 1985.

Hauber and Cullen, "Mutational Analysis of the Trans-Activation-Responsive Region of the Human Immunodeficiency Virus Type I Long Terminal Repeat," *J. Virology*, 62:673, 1988.

Hen et al., "A Mutated Polyoma Virus Enhancer Which is Active in Undifferentiated Embryonal Carcinoma Cells is not Repressed by Adenovirus-2 E1A Products," *Nature*, 321:249, 1986.

Hensel et al., "PMA-Responsive 5' Flanking Sequences of the Human TNF Gene," *Lymphokine Res.*, 8:347, 1989.

Hermonat and Muzyczka, "Use of adeno-associated virus as a mammalian DNA cloning vector; transduction of neomycin resistance into mammalian tissue culture cells," *Proc. Nat'l. Acad. Sci. USA*, 81:6466-6470, 1984.

Herr and Clarke, "The SV40 Enhancer is Composed of Multiple Functional Elements That Can Compensate for One Another," *Cell*, 45:461, 1986.

Hersdorffer et al., "Efficient gene transfer in live mice using a unique retroviral packaging line," *DNA Cell Biol.*, 9:713-723, 1990.

Hilton, Watowich, Katz, Lodish, "Saturation mutagenesis of the WSXWS motif of the erythropoietin receptor," *J. Biol. Chem.*, 271(9):4699-4708, 1996.

Hind, Tennent, Evans, Pepys, "Demonstration of amyloid A (AA) protein and amyloid P component (AP) in deposits of systemic amyloidosis associate with renal adenocarcinoma," *J. Pathology*, 139:159-166, 1983.

Hirochika et al., "Enhancers and Trans-Acting E2 Transcriptional Factors of Papilloma Viruses," *J. Virol.*, 61:2599, 1987.

Hirsch et al., "Identification of Positive and Negative Regulatory Elements Governing Cell-Type-Specific Expression of the Neural-Cell-Adhesion-Molecule Gene," *Mol. Cell. Biol.*, 10:1959, 1990.

Holbrook et al., "cis-Acting Transcriptional Regulatory Sequences in the Gibbon Ape Leukemia Virus (GALV) Long Terminal Repeat," *Virology*, 157:211, 1987.

Horlick and Benfield, "The Upstream Muscle-Specific Enhancer of the Rat Muscle Creatine Kinase Gene is Composed of Multiple Elements," *Mol. Cell. Biol.*, 9:2396, 1989.

Horwich et al. "Synthesis of hepadenovirus particles that contain replication-defective duck hepatitis B virus genomes in cultured HuH7 cells," *J. Virol.*, 64:642-650, 1990.

Houry, Frishman, Eckerskom, Lottspelch, Hartl, "Identification of in vivo substrates of the chaperonin GroEL," *Nature*, 402:147-154, 1999.

Huang et al., "Glucocorticoid Regulation of the Ha-MuSV p21 Gene Conferred by Sequences From Mouse Mammary Tumor Virus," *Cell*, 27:245, 1981.

Huang, Eberstadt, Olejniczak, Meadows, Fesik, "NMR structure and mutagenesis of the Fas (APO-1/CD95) death domain," *Nature*, 384:638-641, 1996.

Hug et al, "Organization of the Murine Mx Gene and Characterization of its Interferon- and Virus-Inducible Promoter," *Mol. Cell. Biol.*, 8:3065, 1988.

Hung et al., "Crystal structure of the ATP-binding subunit of an ABC transporter," *Nature*, 396:703-707, 1998.

Huth, Bewley, Jackson, Hinnebusch, Clore, Gronenbom, "Design of an expression system for detecting folded protein domains and mapping macromolecular interactions by NMR," *Protein Sci.*, (11):2359-2364, 1997.

Hwang et al., "Characterization of the S-Phase-Specific Transcription Regulatory Elements in a DNA-Replication-Independent Testis-Specific H2B (TH2B) Histone Gene," *Mol. Cell. Biol.*, 10:585, 1990.

Imagawa et al., "Transcription Factor AP-2 Mediates Induction by Two Different Signal-Transduction Pathways: Protein Kinase C and cAMP," *Cell*, 51:251, 1987.

Imbra and Karin, "Phorbol Ester Induces the Transcriptional Stimulatory Activity of the SV40 Enhancer," *Nature*, 323:555, 1986.

Imler et al., "Negative Regulation Contributes to Tissue Specificity of the Immunoglobulin Heavy-Chain Enhancer," *Mol. Cell. Biol.*, 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.*, 4:875, 1984.

Inouye et al., "Up-promoter mutations in the lpp gene of *Escherichia coli*," *Nucl. Acids Res.*, 13:3101-3109, 1985.

Jakobovits et al., "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.*, 8:2555, 1988.

Jameel and Siddiqui, "The Human Hepatitis B Virus Enhancer Requires Transacting Cellular Factor(s) for Activity," *Mol. Cell. Biol.*, 6:710, 1986.

Jaynes et al, "The Muscle Creatine Kinase Gene is Regulated by Multiple Upstream Elements, Including a Muscle-Specific Enhancer," *Mol. Cell. Biol.*, 8:62, 1988.

Johnson et al., "Muscle Creatine Kinase Sequence Elements Regulating Skeletal and Cardiac Muscle Expression in Transgenic Mice," *Mol. Cell. Biol.*, 9:3393, 1989.

Jones and Shenk, "Isolation of deletion and substitution mutants of adenovirus type 5," *Cell*, 13:181-188, 1978.

Kadesch and Berg, "Effects of the Position of the Simian Virus 40 Enhancer on Expression of Multiple Transcription Units in a Single Plasmid," *Mol. Cell. Biol.*, 6:2593, 1986.

Kaneda et al., "Increased expression of DNA cointroduced with nuclear protein in adult rat liver," *Science*, 243:375-378, 1989.

Kaplitt et al., "Long-term gene expression and phenotypic correction suing adeno-associated virus vectors in the mammalian brain," *Nature Genetics*, 8:148-154, 1994.

Kapust and Waugh, *Protein Science*, 8:1668-1674, 1999.

Karin et al., "Metal-Responsive Elements Act as Positive Modulators of Human Metallothionein-IIA Enhancer Activity," *Mol. Cell. Biol.*, 7:606, 1987.

Karlsson et al., *EMBO J*, 5:2377-2385, 1986.

Kasahara et al., *Science*, 266:1373-1376, 1994. askind et al., "Dependence of moloney murine leukemia virus production on cell growth," *Virology*, 67:242-248, 1975.

Katinka et al., "Expression of Polyoma Early Functions in Mouse Embryonal Carcinoma Cells Depends on Sequence Rearrangements in the Beginning of the Late Region," *Cell*, 20:393, 1980.

Katinka et al., "Polyoma DNA Sequences Involved in the Control of Viral Gene Expression in Murine Embryonal Carcinoma Cells," *Nature*, 290:720, 1981.

Kato et al., "Expression of hepatitis β virus surface antigen in adult rat liver," *J. Biol. Chem.*, 266:3361-3364, 1991.

Kaufman, "Selection and Coamplification of Heterologous Genes in Mammalian Cells," *Methods in Enzymology*, 185:537-566, 1990.

Kawaguchi et al., "CAG expansions in a novel gene for Machado-Joseph disease at chromosome 14q32.1," *Nature Genetics*, 8:221-228, 1994.

Kawamoto et al., "Identification of the Human Beta-Actin Enhancer and its Binding Factor," *Mol. Cell. Biol.*, 8:267, 1988.

Kelleher and Vos, "Long-term episomal gene delivery in human lymphoid cells using human and avian adenoviral-assisted transfection," *Biotechniques*, 17(6):1110-1117, 1994.

Kiledjian et al., "Identification and Characterization of Two Functional Domains Within the Murine Heavy-Chain Enhancer," *Mol. Cell. Biol.*, 8:145, 1988.

King and Sorscher, "Recombinant synthesis of cystic fibrosis transmembrane conductance regulator and functional nucleotide-binding domains," *Methods Enzymol.*, 292:686-697, 1998.

Klamut et al., "Molecular and Functional Analysis of the Muscle-Specific Promoter Region of the Duchenne Muscular Dystrophy Gene," *Mol. Cell. Biol.*, 10:193, 1990.

Klein et al., "High-velocity microprojectiles for delivering nucleic acids into living cells," *Nature*, 327:70-73, 1987.

Ko, Thomas, Delannoy, Pedersen, "The cystic fibrosis transmembrane conductance regulator. Overexpression, purification, and characterization of wild type and F508 mutant forms of the first nucleotide binding fold in fusion with the maltose-binding protein," *J. Biol. Chem.*, 268:24330-24338, 1993.

Koch et al., "Anatomy of a New B-Cell-Specific Enhancer," *Mol. Cell. Biol.*, 9:303, 1989.

Koller, Smithies, "Altering genes in animals by gene targeting," *Annu. Rev. Immunol.*, 10:705-730, 1992.

Koncz, Mayerhofer, Koncz-Kalman, Nawrath, Reiss, Redei, Schell, "Isolation of a gene encoding a novel chloroplast protein by T-DNA tagging in *Arabidopsis thaliana*, *EMBO J*, (5):1337-1346, 1990.

Kotin et al., "Site-specific integration by adeno-associated virus," *Proc. Natl. Acad. Sci. USA*, 87:2211-2215, 1990.

Krause, Holtmann, Eickemeier, Winzen, Szamel, Resch, Saklatvala, Kracht, "Stress-activated protein kinase/Jun N-terminal kinase is required for interleukin (IL)-1-induced IL-6 and IL-8 gene expression in the human epidermal carcinoma cell line KB," *J. Biol. Chem.*, 273(37):23681-23689, 1998.

Kriegler et al., "A Novel Form of TNF/Cachectin Is a Cell-Surface Cytotoxix Transmembrane Protein: Ramifications for the Complex Physiology of TNF," *Cell*, 53:45, 1988.

Kriegler et al., "Promoter Substitution and Enhancer Augmentation Increases the Penetrance of the SV40 A Gene to Levels Comparable to That of the Harvey Murine Sarcoma Virus Ras Gene in Morphologic Transformation," In: *Gene Expression*, eds. D. Hamer and M. Rosenberg. New York: Alan R. Liss, 1983.

Kriegler et al., "Transformation Mediated by the SV40 T Antigens: Separation of the Overlapping SV40 Early Genes with a Retroviral Vector," *Cell*, 38:483, 1984a.

Kriegler et al., "Viral Integration and Early Gene Expression Both Affect the Efficiency of SV40 Transformation of Murine Cells: Biochemical and Biological Characterization of an SV40 Retrovirus," In: *Cancer Cells 2/Oncogenes and Viral Genes*, Van de Woude et al. eds, Cold Spring Harbor: Cold Spring Harbor Laboratory, 1984b.

Kuhl et al., "Reversible Silencing of Enhancers by Sequences Derived From the Human IFN-alpha Promoter," *Cell*, 50:1057, 1987.

Kunz et al., "Identification of the Promoter Sequences Involved in the Interleukin-6-Dependent Expression of the Rat Alpha-2-Macroglobulin Gene," *Nucl. Acids Res.*, 17:1121, 1989.

La Spada, Wilson, Lubahn, Harding, Fischbeck, "Androgen receptor gene mutations in X-linked spinal and bulbar muscular atrophy," *Nature*, 352:77-79, 1991.

LaFace et al., "Gene transfer into hematopoietic progenitor cells mediated by an adeno-associated virus vector," *Viology*, 162:483-486, 1988.

Lambert and Borek, "X-ray-induced changes in gene expression in normal and oncogene-transformed rat cell lines," *J. Natl. Cancer Inst.*, 80(18):1492-1497, 1988.

Lareyre, Thomas, Zheng, Kasper, Ong, Orgebin-Crist, Matusik, "A 5-kilobase pair promoter fragment of the murine epididymal retinoic acid-binding protein gene drives the tissue-specific, cell-specific, and androgen-regulated expression of a foreign gene in the epididymis of transgenic mice," *J. Biol. Chem.*, 274(12):8282-8290, 1999.

Larsen et al., "Repression Medaites Cell-Type-Specific Expression of the Rat Growth Hormone Gene," *Proc. Natl. Acad. Sci. U.S.A.*, 83:8283, 1986.

Laspia et al., "HIV-1 Tat Protein Increases Transcriptional Initiation and Stabilizes Elongation," *Cell*, 59:283, 1989.

Latimer et al., "Highly Conserved Upstream Regions of the $\alpha_1$-Antitrypsin Gene in Two Mouse Species Govern Liver-Specific Expression by Different Mechanisms," *Mol. Cell. Biol.*, 10:760, 1990.

Laughlin et al., "Latent Infection of KB Cells with Adeno-Associated Virus Type 2," *J. Virol.*, 60:515-524, 1986.

Lebkowski et al., "Adeno-associated virus: a vector system for efficient introduction and integration of DNA into a variety of mammalian cell types," *Mol. Cell. Biol.*, 8:3988-3996, 1988.

Lee et al., "Glucocorticoids Regulate Expression of Dihydrofolate Reductase cDNA in Mouse Mammary Tumor Virus Chimaeric Plasmids," *Nature*, 294:228, 1981.

Lee, Choi, Yu, "Effect of the N-terminal hydrophobic sequence of hepatitis B virus antigen on the folding and assembly of hybrid beta-galactosidase in *Escherichia coli*," *Eur. J. Biochem.*, 187:417-424, 1990.

Lee, Wang, Yajima, Jose, Mouradian, "Tissue-specific promoter usage in the D1A dopamine receptor gene in brain and kidney," *DNA Cell Biol.*, (11):1267-1275, 1997.

Levenson et al., "Internal ribosomal entry site-containing retroviral vectors with green fluorescent protein and drug resistance markers," *Human Gene Therapy*, 9:1233-1236, 1998.

Levinson et al., "Activation of SV40 Genome by 72-Base-Pair Tandem Repeats of Moloney Sarcoma Virus," *Nature*, 295:79, 1982.

Levrero et al., "Defective and nondefective adenovirus vectors for expressing foreign genes in vitro and in vivo," *Gene*, 101:195-202, 1991.

Lin et al., "Delineation of an Enhancerlike Positive Regulatory Element in the Interleukin-2 Receptor $\alpha$-Chain Gene," *Mol. Cell. Biol.*, 10:850, 1990.

Luo et al., "Adeno-associated virus 2 mediated transfer and functional expression of a gene encoding the human granulocyte-macrophage colony-stimulating factor," *Blood*, 82 (Supp.): 1,303A, 1994.

Luria et al., "Promoter Ehancer Elements in the Rearranged Alpha-Chain Gene of the Human T-Cell Receptor," *EMBO J*, 6:3307, 1987.

Lusky and Botchan, "Transient Replication of Bovine Papilloma Virus Type 1 Plasmids: cis and trans Requirements," *Proc. Natl. Acad. Sci. U.S.A.*, 83:3609, 1986.

Macejak and Sarnow, "Internal initiation of translation mediated by the 5' leader of a cellular mRNA," *Nature*, 353:90-94, 1991.

Majors and Varmus, "A Small Region of the Mouse Mammary Tumor Virus Long Terminal Repeat Confers Glucocorticoid Hormone Regulation on a Linked Heterologous Gene," *Proc. Natl. Acad. Sci. U.S.A.*, 80:5866, 1983.

Mann et al., "Construction of a retrovirus packaging mutant and its use to produce helper-free defective retrovirus," *Cell*, 33:153-159, 1983.

Markowitz et al., "A safe packaging line for gene transfer: Separating viral genes on two different plasmids," *J. Virol.*, 62:1120-1124, 1988.

Marks, Esch, Herman, Sivakumaran, Oppenheimer, "A model for cell-type determination and differentiation in plants," *Symp Soc Exp Biol*, 45:77-87, 1991.

Martin and Gusella, "Huntington's disease: pathogenesis and management," *N. Engl. J. Med.*, 315:1267-1276, 1986.

Maxwell, Mittermaier, Forman-Kay, Davidson, "A simple in vivo assay for increased protein solubility," *Protein Science*, 8:1908-1911, 1999.

McCann, Choi, Yamasaki, Ames, "Detection of carcinogens as mutagens in the Salmonella/microsome test: assay of 300 chemicals," Proc. Natl. Acad. Sci. U.S.A., (12):5135-5139, 1975.

McCarty et al., "Sequences Required for Coordinate Induction of Adeno-Associated Virus p19 and p40 Promoters by Rep Protein," J. Virol., 65:2936-2945, 1991.

McLaughlin et al., "Adeno-Associated Virus General Transduction Vectors: Analysis of Proviral Structures," J. Virol., 62:1963-1973, 1988.

McNeall et al., "Hyperinducible Gene Expression From a Metallotionein Promoter Containing Additional Metal-Responsive Elements," Gene, 76:81, 1989.

Miksicek et al., "Glucocorticoid Responsiveness of the Transcriptional Enhancer of Moloney Murine Sarcoma Virus," Cell, 46:203, 1986.

Miller, Curr. Top. Microbiol. Immunol., 158:1, 1992.

Mordacq and Linzer, "Co-localization of Elements Required for Phorbol Ester Stimulation and Glucocorticoid Repression of Proliferin Gene Expression," Genes and Dev., 3:760, 1989.

Moreau et al., "The SV40 Base-Repair Repeat Has a Striking Effect on Gene Expression Both in SV40 and Other Chimeric Recombinants," Nucl. Acids Res., 9:6047, 1981.

Musesing et al., "Regulation of mRNA Accumulation by a Human Immunodeficiency Virus Trans-Activator Protein," Cell, 48:691, 1987.

Muzyczka, "Use of Adeno-Associated Virus as a General Transduction Vector for Mammalian Cells," Curr. Top. Microbiol. Immunol., 158:97-129, 1992.

Ng et al., "Regulation of the Human Beta-Actin Promoter by Upstream and Intron Domains," Nuc. Acids Res., 17:601, 1989.

Nicolas and Rubinstein, "Retroviral vectors," In: Vectors: A survey of molecular cloning vectors and their uses, Rodriguez and Denhardt (eds.), Stoneham: Butterworth, pp. 494-513, 1988.

Nicolau and Sene, "Liposome-mediated DNA transfer in eukaryotic cells: dependence of the transfer efficiency upon the type of liposomes used and the host cell cycle stage," Biochim. Biophys. Acta, 721:185-190, 1982

Nicolau et al., "Liposomes as carriers for in vivo gene transfer and expression," Methods Enzymol., 149:157-176, 1987.

Nomoto, Tatematsu, Takahashi, Osada, "Cloning and characterization of the alternative promoter regions of the human LIMK2 gene responsible for alternative transcripts with tissue-specific expression," Gene, 236(2):259-71, 1999.

Ohi et al., "Construction and replication of an adeno-associated virus expression vector that contains human λ-globin cDNA," Gene, 89L:279-282, 1990.

Ondek et al., "Discrete Elements Within the SV40 Enhancer Region Display Different Cell-Specific Enhancer Activities," EMBO J, 6:1017, 1987.

Oppenheimer, Herman, Sivakumaran, Esch, Marks, "A myb gene required for leaf trichome differentiation in Arabidopsis is expressed in stipules," Cell, 67(3):483493, 1991.

Ornitz et al., "Promoter and Enhancer Elements From the Rat Elastase I Gene Function Independently of Each Other and of Heterologous Enhancers," Mol. Cell. Biol., 7:3466, 1987.

Palmiter et al., "Differential Regulation of Metallothionein-Thymidine Kinase Fusion Genes in Transgenic Mice and Their Offspring," Cell, 29:701, 1982.

Papouchado, Valdez, Ghiringhelli, Poskus, Ermacora, Eur. J. Biochem., 246:350-359, 1997.

Pech et al., "Functional Identification of Regulatory Elements Within the Promoter Region of Platelet-Derived Growth Factor 2," Mol. Cell. Biol., 9:396, 1989.

Pecorari, Minard, Desmadril, Yon, Structure and functional complementation of engineered fragments from yeast phosphoglycerate kinase," Protein Engineering, 6:313-325, 1993.

Perales, Ferkol, Beegen, Ratnoff, Hanson, "Gene transfer in vivo: sustained expression and regulation of genes introduced into the liver by receptor-targeted uptake," Proc. Natl. Acad. Sci. USA, 91(9):4086-4090, 1994.

Perez-Stable and Constantini, "Roles of Fetal γ-globin Promoter Elements and the Adult β-globin 3' Enhancer in the Stage-Specific Expression of Globin Genes," Mol. Cell. Biol., 10:1116, 1990.

Picard and Schaffner, "A lymphocyte-specific enhancer in the mouse immunoglobulin kappa gene," Nature, 307:83, 1984.

Pinkert et al., "An albumin enhancer located 10 kb upstream functions along with its promoter to direct efficient, liver-specific expression in transgenic mice," Genes and Dev., 1:268, 1987.

Ponta et al., "Hormonal response region in the mouse mammary tumor virus long terminal repeat can be dissociated from the proviral pomoter and has enhancer properties," Proc. Natl. Acad. Sci. U.S.A., 82:1020, 1985.

Porton et al., "Immunoglobulin Heavy-Chain Enhancer is Required to Maintain Transfected γ2A Gene Expression in a pre-B-cell Line," Mol. Cell. Biol., 10: 1076, 1990.

Potter et al., "Enhancer-dependent expression of human k immunoglobulin genes introduced into mouse pre-B lymphocytes by electroporation," Proc. Natl. Acad. Sci. USA, 81:7161-7165, 1984.

PPelletier and Sonenberg, "Internal initiation of translation of eukaryotic mRNA directed by a sequence derived from poliovirus RNA," Nature, 334:320-325, 1988.

Qu and Thomas, "Alteration of the cystic fibrosis transmembrane conductance regulator folding pathway," J. Biol. Chem., 271(13):7261-7264, 1996.

Queen and Baltimore, "Immunoglobulin Gene Transcription is Activated by Downstream Sequence Elements," Cell, 35:741, 1983.

Quinn et al., "Multiple Components are Required for Sequence Recognition of the AP1 Site in the Gibbon Ape Leukemia Virus Enhancer," Mol. Cell. Biol., 9:4713, 1989.

Racher et al., Biotechnology Techniques, 9:169-174, 1995.

Rao, Cohen, Oprian, "Rhodopsin mutation G90D and a molecular mechanism for congenital night blindness," Nature, 367:639-642, 1994.

Redondo et al., "A T-Cell-Specific Transcriptional Enhancer Within the Human T-Cell Receptor δ Locus," Science, 247:1225, 1990.

Reisman and Rotter, "Induced Expression From the Moloney Murine Leukemia Virus Long Terminal Repeat During Differentiation of Human Myeloid Cells is Mediated Through its Transcriptional Enhancer," Mol. Cell. Biol., 9:3571, 1989.

Renan, "Cancer genes: current status, future prospects, and applicants in radiotherapy/oncology," Radiother. Oncol., 19:197-218, 1990.

Resendez Jr. et al., "Identification of Highly Conserved Regulatory Domains and Protein-Binding Sites in the Promoters of the Rat and Human Genes Encoding the Stress-Inducible 78-kilodalton Glucose-Regulated Protein," Mol. Cell. Biol., 8:4579, 1988.

Richards and Vithayatil, "The preparation of subtilisin-modified ribonuclease and the separation of the peptide and protein components," *J. Biol. Chem.*, 234:1459-1465, 1959.

Ridgeway, "Mammalian expression vectors," In: *Vectors: A survey of molecular cloning vectors and their uses*. Rodriguez and Denhardt, eds. Stoneham: Butterworth, pp. 467-492, 1988.

Ripe et al., "Regulatory Elements in the 5' Flanking Region and the First Intron Contribute to Transcriptional Control of the Mouse alpha-1-type Collagen Gene," *Mol. Cell. Biol.*, 9:2224, 1989.

Rippe et al., "DNA-mediated gene transfer into adult rat hepatocytes in primary culture," *Mol. Cell. Biol.*, 10:689-695, 1990.

Rittling et al., "AP-1/jun-binding Sites Mediate Serum Inducibility of the Human Vimentin Promoter," *Nuc. Acids Res.*, 17:1619, 1989.

Rosen et al., "The Location of cis-acting Regulatory Sequences in the Human T-Cell Lymphotropic Virus Type III (HTLV-111/LAV) Long Terminal Repeat," *Cell*, 41:813, 1988.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079-9083, 1989.

Sambrook, Fritsch, Maniatis, *Molecular Cloning: A Laboratory Manual*, 2nd Ed., Cold Spring Harbor Press, Cold Spring Harbor, N.Y., 1989.

Samulski et al., "Helper-free stocks of recombinant adeno-associated viruses: Normal integration does not require viral gene expression," *J. Virol.*, 63:3822-3828, 1989.

Samulski et al., "Targeted integration of adeno-associated virus (AAV) into human chromosome 19," *EMBO J*, 10:3941-3950, 1991.

Santerre, Allen, Hobbs Jr, Rao, Schmidt, "Expression of prokaryotic genes for hygromycin B and G418 resistance as dominant-selection markers in mouse L cells," *Gene*, (1-3):147-156, 1984.

Satake et al., "Biological Activities of Oligonucleotides Spanning the F9 Point Mutation Within the Enhancer Region of Polyoma Virus DNA," *J. Virology*, 62:970, 1988.

Schaffner et al., "Redundancy of Information in Enhancers as a Principle of Mammalian Transcription Control," *J. Mol. Biol.*, 201:81, 1988.

Schagger and von Jagow, "Tricine-sodium dodecyl sulfate-polyacrylamide gel electrophoresis for the separation of proteins in the range from 1 to 100 kDa," *Anal. Biochem.*, 166(2):368-379, 1987.

Schmidt, Burr, Burr, "Transposon tagging and molecular analysis of the maize regulatory locus opaque-2," *Science*, 238(4829):960-963, 1987.

Schonberger, Knox, Bibi, Pines, "Split invertase polypeptides form functional complexes in the yeast periplasm in vivo," *Proc. Natl. Acad. Sci. USA.*, 93:9612-9617, 1996.

Searle et al., "Building a Metal-Responsive Promoter With Synthetic Regulatory Elements," *Mol. Cell. Biol.*, 5:1480, 1985.

Shallom et al., "Essential protein-protein interactions between *Plasmodium falciparum* thymidylate synthase and dihydrofolate reductase domains" *J. Biol. Chem.* 274:37781-37786, 1999.

Sharp and Marciniak, "HIV Tar: an RNA Enhancer?," *Cell*, 59:229, 1989.

Shaul and Ben-Levy, "Multiple Nuclear Proteins in Liver Cells are Bound to Hepatitis B Virus Enhancer Element and its Upstream Sequences," *EMBO J.*, 6:1913, 1987.

Shelling, Smith, "Targeted integration of transfected and infected adeno-associated virus vectors containing the neomycin resistance gene," *Gene Ther.*, (3):165-169, 1994.

Sherman et al., "Class II Box Consensus Sequences in the HLA-DRA Gene: Transcriptional Function and Interaction with Nuclear Proteins," *Mol. Cell. Biol.*, 9:50, 1989.

Sleigh and Lockett, "SV40 Enhancer Activation During Retinoic-Acid-Induced Differentiation of F9 Embryonal Carcinoma Cells," *J. EMBO*, 4:3831, 1985.

Sommer Beltran, Huijser, Pape, Lonnig, Saedler, Schwarz-Sommer, "Deficiens, a homeotic gene involved in the control of flower morphogenesis in *Antirrhinum majus*: the protein shows homology to transcription factors," *EMBO J.*, 9(3):605-613, 1990

Spalholz et al., "Transactivation of a Bovine Papilloma Virus Transcriptional Regulatory Element by the E2 Gene Product," *Cell*, 42:183, 1985.

Spandau and Lee, "Trans-Activation of Viral Enhancers by the Hepatitis B Virus X Protein," *J. Virology*, 62:427, 1988.

Spandidos and Wilkie, "Host-Specificities of Papilloma Virus, Moloney Murine Sarcoma Virus and Simian Virus 40 Enhancer Sequences," *EMBO J.*, 2:1193, 1983.

Stephens and Hentschel, "The Bovine Papilloma Virus Genome and its Uses as a Eukaryotic Vector," *Biochem. J*, 248:1, 1987.

Stuart et al., "Identification of Multiple Metal Regulatory Elements in Mouse Metallothionein-I Promoter by Assaying Synthetic Sequences," *Nature*, 317:828, 1985.

Sugihara and Baldwin, "Effects of 3' end deletions from *Vibrio* hrveyi luxB gene on luciferase subunit folding and enzyme assembly: generation of temperature-sensitive polypeptide folding mutants," *Biochemistry*, 27:2872-2880, 1988.

Sullivan and Peterlin, "Transcriptional Enhancers in the HLA-DQ Subregion," *Mol. Cell. Biol.*, 7:3315, 1987.

Swartzendruber and Lehman, "Neoplastic Differentiation: Interaction of Simian Virus 40 and Polyoma Virus with Murine Teratocarcinoma Cells," *J. Cell. Physiology*, 85:179, 1975.

Takebe et al., "SRα Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell. Biol.*, 8:466, 1988.

Tan and Pepys, "Amyloidosis," *Histopathology*, 25:403-414, 1994.

Taniuchi and Anfinsen, "Simultaneous formation of two alternative enzymology active structures by complementation of two overlapping fragments of staphylococcal nuclease," *J. Biol. Chem.*, 246:2291-1301, 1971.

Tavernier et al., "Deletion Mapping of the Inducible Promoter of Human IFN-beta Gene," *Nature*, 301:634, 1983.

Taylor and Kingston, "E1a Trans-Activation of Human HSP70 Gene Promoter Substitution Mutants is Independent of the Composition of Upstream and TATA Elements," *Mol. Cell. Biol.*, 10:176, 1990b.

Taylor and Kingston, "Factor Substitution in a Human HSP70 Gene Promoter: TATA-Dependent and TATA-Independent Interactions," *Mol. Cell. Biol.*, 10:165, 1990a.

Taylor et al., "Stimulation of the Human Heat-Shock Protein 70 Promoter in vitro by Simian Virus 40 Large T Antigen," *J. Biol. Chem.*, 264:15160, 1989.

Temin, "Retrovirus vectors for gene transfer: Efficient integration into and expression of exogenous DNA in vertebrate cell genome," In: *Gene Transfer*, Kucherlapati (ed.), New York: Plenum Press, pp. 149-188, 1986.

The Huntington's Disease Collaborative Research Group. A novel gene containing a trinucleotide repeat that is expanded and unstable on Huntington's disease chromosomes, *Cell*, 72:971-983, 1993.

Thiesen et al., "A DNA Element Responsible for the Different Tissue Specificities of Friend and Moloney Retroviral Enhancers," *J. Virology*, 62:614, 1988.

Thomas, Ko, Pedersen, "Altered protein folding may be the molecular basis of most cases of cystic fibrosis," *FEBS Lett.*, 312:7-9, 1992.

Thomas, Qu, Pedersen, "Defective protein folding as a basis of human disease," *TIBS* 20, 456-459, 1995.

Tratschin et al., "A human parvovirus, adeno-associated virus, as a eucaryotic vector: transient expression and encapsidation of the procaryotic gene for chloramphenicol acetyltransferase," *Mol. Cell. Biol.*, 4:2072-2081, 1984.

Tratschin et al., "Adeno-associated virus vector for high-frequency integration, expression and rescue of genes in mammalian cells," *Mol. Cell. Biol.*, 5:32581-3260, 1985.

Treisman, "Transient Accumulation of c-fos RNA Following Serum Stimulation Requires a Conserved 5' Element and c-fos 3' Sequences," *Cell*, 42:889, 1985.

Tronche et al., "Anatomy of the Rat Albumin Promoter," *Mol. Biol. Med.*, 7:173, 1990.

Tronche et al., "The Rat Albumin Promoter: Cooperation with Upstream Elements is Required When Binding of APF/INF 1 to the Proximal Element is Partially Impaired by Mutation or Bacterial Methylation," *Mol. Cell. Biol.*, 9:4759, 1989.

Trudel and Constantini, "A 3' Enhancer Contributes to the Stage-Specific Expression of the Human Beta-Globin Gene," *Genes and Dev.*, 6:954, 1987.

Tsumaki, Kimura, Tanaka, Kimura, Ochi, Yamada, "Modular arrangement of cartilage- and neural tissue-specific cis-elements in the mouse alpha2(XI) collagen promoter," *J. Biol. Chem.*, 273(36):22861-22864, 1998.

Tur-Kaspa et al., "Use of electroporation to introduce biologically active foreign genes into primary rat hepatocytes," *Mol. Cell. Biol.*, 6:716-718, 1986.

Tyndall et al., "A Region of the Polyoma Virus Genome Between the Replication Origin and Late Protein-Coding Sequences is Required in cis for Both Early Gene Expression and Viral DNA Replication," *Nuc. Acids. Res.*, 9:6231, 1981.

Vannice and Levinson, "Properties of the Human Hepatitis B Virus Enhancer: Position Effects and Cell-Type Nonspecificity," *J. Virology*, 62:1305, 1988.

Vasseur et al., "Isolation and Characterization of Polyoma Virus Mutants Able to Develop in Multipotential Murine Embryonal Carcinoma Cells," *Proc. Natl. Acad. Sci. U.S.A.*, 77:1068, 1980.

Wagner et al., *Science*, 260:1510-1513, 1990.

Waldo, Standish, Berendzen, Terwilliger, "Rapid protein-folding assay using green fluorescent protein," *Nature Biotechnology*, 17:691-695, 1999.

Walsh et al., "Phenotypic correction of Fanconi anemia in human hematopoietic cells with a recombinant adeno-associated virus vector," *J. Clin. Invest.*, 94:1440-1448, 1994.

Wang et al., *Biochimica et Biophysica Acta* 888(2):225-36, 1986.

Wang, Castro, Wilkes, Altenberg, *Biochem J.*, 338:77-81, 1999.

Warren, Marolewski, Benkovic, "A rapid screen of active site mutants in glycinamide ribonucleotide transformylase," *Biochemistry*, 35(27):8855-8862, 1996.

Weber et al., "An SV40 'Enhancer Trap' Incorporates Exogenous Enhancers or Generates Enhancers From its Own Sequences," *Cell*, 36:983, 1984.

Wei et al., "Expression of the human glucocerebrosidase and arylsulfatase A genes in murine and patient primary fibroblasts transduced by an adeno-associated virus vector," *Gene Therapy*, 1:261-268, 1994.

Weinberger et al. "Localization of a Repressive Sequence Contributing to B-cell Specificity in the Immunoglobulin Heavy-Chain Enhancer," *Mol. Cell. Biol.*, 8:988, 1984.

Wells and Warren (eds.), "Genetic instabilities and hereditary neurological diseases," *Am J. Hum. Genet.*, 63(6):1921, 1998.

Ullmann, Jacob, Monod, "Characterization by in vitro Complementation of a Peptide corresponding to an Operator-proximal Segment of the β-Galactosidase Structural Gene of *Excherichia coli*," *J. Mol. Biol.*, 24:339-343, 1967.

Winoto and Baltimore, "αβ-lineage-specific Expression of the α T-Cell Receptor Gene by Nearby Silencers," *Cell*, 59:649, 1989.

Witte, Fuks, Haimovitz-Friedman, Vlodavsky, Goodman, Eldor, 'Effects of irradiation on the release of growth factors from cultured bovine, porcine, and human endothelial cells," *Cancer Res.*, 49(18):5066-5072, 1989.

Wong et al., "Appearance of β-lactamase activity in animal cells upon liposome mediated gene transfer," *Gene*, 10:87-94, 1980.

Wood, Wetzel, Martin, Hurle, "Prolines and amyloidogenicity in fragments of the Alzheimer's peptide beta/A4," *Biochemistry*, 34(3):724-730, 1995.

Wu, Squire, Song, Weksberg, "Promoter-dependent tissue-specific expressive nature of imprinting gene, insulin-like growth factor in human tissues," *Biochem. Biophys. Res. Commun.*, 233(1):221-226, 1997.

Wu and Wu, "Receptor-mediated in vitro gene transfections by a soluble DNA carrier system," *J. Biol. Chem.*, 262:4429-4432, 1987.

Wu and Wu, *Adv. Drug Delivery Rev.*, 12:159-167, 1993.

Wynn, Davie, Cox, Chuang, "Chaperonins groEL and groES promote assembly of heterotetramers (alpha 2 beta 2) of mammalian mitochondrial brandhed-chain alpha-keto acid decarboxylase in *Escherichia coli*," *J. Biol. Chem.*, 267:12400-12403, 1992.

Yang et al., "Characterization of cell lines that inducibly express the adeno-associated virus Rep proteins," *J. Virol.*, 68:4847-4856, 1994.

Yang et al., "In vivo and in vitro gene transfer to mammalian somatic cells by particle bombardment," *Proc. Nat'l Acad. Sci. USA*, 87:9568-9572, 1990.

Yanisch-Perron et al., "Improved M13 phage cloning vectors and host strains: nucleotide sequences of the M13 mp and pUC19 vectors", *Gene.*, 33(1):103-119, 1985.

Yelton, Rosok, Cruz, Cosand, Bajorath, Hellstrom, Hellstrom, Huse, Glaser, "Affinity maturation of the BR96 anti-carcinoma antibody by codon-based mutagenesis," *J. Immunol.*, 155(4):1994-2004, 1995.

Yoder et al., "In vivo gene transfer in murine hematopoietic reconstituting stem cells mediated by the adeno-associated virus 2-based vectors," *Blood*, 82 (Supp.): 1:347A, 1994.

Yutzey et al. "An Internal Regulatory Element Controls Troponin I Gene Expression," *Mol. Cell. Biol.*, 9:1397, 1989.

Zabin and Villarejo, "Protein complementation," *Annu. Rev. Biochem.*, 44:296-314, 1975.

Zeng, Ye, Larson, "Repressor for the sn-glycerol 3-phosphate regulon of *Escherichia coli* K-12: primary structure and identification of the DNA-binding domain," *J. Bacteriol.,* 178(24):7080-7089, 1996.

Zhao-Emonet, Boyer, Cohen, Klatzrnann, "Deletional and mutational analyses of the human CD4 gene promoter: characterization of a minimal tissue-specific promoter," *Biochim. Biophys. Acta.,* 1442(2-3):109-119, 1998.

Zhou et al., "Adeno-associated virus 2 mediated gene transfer in murine hematopoietic cells, *Exp. Hematol.* (NY), 21:928-933, 1993.

Zhou, et al., "Adeno-associated virus 2-mediated high efficiency gene transfer into immature and mature subsets of hematopoietic progenitor cells in human umbilical cord blood," *J. Exp. Med.,* 179:1867-1875, 1994.

What is claimed is:

1. A method for screening a candidate modulator substance for modulation of protein folding and/or solubility comprising:
   a) providing an expression construct comprising (i) a gene encoding fusion protein, said fusion protein comprising a protein of interest fused to a first segment of a marker protein, wherein said first segment exhibits only systematic effects on the folding or solubility of the protein of interest, and (ii) a promoter active in said host cell and operably linked to said gene;
   b) contacting said fusion protein with a second segment of said marker protein, wherein said second segment is capable of structural complementation with said first segment, wherein contacting takes place in the presence of said candidate modulator substance; and
   c) determining structural complementation,
   wherein a relative change in structural complementation, as compared to the structural complementation observed in the absence of said candidate modulator substance, indicates that said candidate modulator substance is a modulator of protein folding and/or solubility.

2. The method of claim 1, wherein said fusion is C-terminal to said protein of interest.

3. The method of claim 1, wherein said fusion is N-terminal to said protein of interest.

4. The method of claim 1, wherein said marker protein is selected from the group consisting of a target binding protein, an enzyme, a protein inhibitor, a chromophore.

5. The method of claim 1, wherein said host cell is selected from the group consisting of a bacterial cell, an insect cell, a yeast cell, a nematode cell, a mammalian cell.

6. The method of claim 1, wherein said candidate modulator substance is selected from the group consisting of a protein, a nucleic acid or a small molecule.

* * * * *

UNITED STATES PATENT AND TRADEMARK OFFICE
CERTIFICATE OF CORRECTION

| | | |
|---|---|---|
| PATENT NO. | : 7,635,569 B2 | Page 1 of 1 |
| APPLICATION NO. | : 11/617191 | |
| DATED | : December 22, 2009 | |
| INVENTOR(S) | : Philip Jordan Thomas | |

It is certified that error appears in the above-identified patent and that said Letters Patent is hereby corrected as shown below:

In column 1, lines 18-20, delete
"The invention disclosed herein was made with the support of the U.S. Government under The National Institutes of Health Grant DK49835.".

In claim 1, column 61, line 58, delete "modulation" and insert --modulating-- therefor.

Signed and Sealed this

Thirtieth Day of March, 2010

David J. Kappos
*Director of the United States Patent and Trademark Office*